United States Patent
Wham et al.

(10) Patent No.: US 7,901,400 B2
(45) Date of Patent: Mar. 8, 2011

(54) METHOD AND SYSTEM FOR CONTROLLING OUTPUT OF RF MEDICAL GENERATOR

(75) Inventors: Robert H. Wham, Boulder, CO (US); Chelsea Shields, Boulder, CO (US); Philip M. Tetzlaff, Lafayette, CO (US); Jeremy S. James, Westminster, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1263 days.

(21) Appl. No.: 11/044,805

(22) Filed: Jan. 27, 2005

(65) Prior Publication Data

US 2005/0203504 A1    Sep. 15, 2005

Related U.S. Application Data

(63) Continuation-in-part of application No. 10/427,832, filed on May 1, 2003, now Pat. No. 7,137,980, which is a continuation-in-part of application No. 10/073,761, filed on Feb. 11, 2002, now Pat. No. 6,796,981, which is a continuation-in-part of application No. 09/408,944, filed on Sep. 30, 1999, now Pat. No. 6,398,779.

(60) Provisional application No. 60/105,417, filed on Oct. 23, 1998, provisional application No. 60/539,804, filed on Jan. 27, 2004.

(51) Int. Cl.
*A61B 18/10* (2006.01)
(52) U.S. Cl. ............................................. 606/34; 606/42
(58) Field of Classification Search .............. 606/32–34, 606/40–42
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |

(Continued)

FOREIGN PATENT DOCUMENTS

DE    179607    3/1905

(Continued)

OTHER PUBLICATIONS

International Search Report EP 07008207.8 dated Sep. 5, 2007.

(Continued)

*Primary Examiner* — Michael Peffley

(57) ABSTRACT

A system and method are provided for controlling an electrosurgical generator generating electrosurgical energy which is delivered to a patient for performing an electrosurgical procedure for sealing tissue. The system includes a control module executable on a processor for receiving sensed data corresponding to at least one physical or electrical property related to delivery of the electrosurgical energy. The control module processes the received sensed data and controls the electrosurgical generator including generating at least one corresponding control signal in accordance with the processed sensed data for regulating electrosurgical energy output from the electrosurgical generator. The controlling the electrosurgical generator further includes regulating at least one control variable, a respective control variable of the at least one control variable corresponding to sensed data corresponding to a property of the at least one physical or electrical property to follow at least one mapping for optimizing the tissue sealing.

35 Claims, 15 Drawing Sheets

U.S. PATENT DOCUMENTS

| | | |
|---|---|---|
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,237,891 A | 12/1980 | DuBose et al. |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |

| | | | | | | |
|---|---|---|---|---|---|---|
| 4,818,954 A | 4/1989 | Flachenecker et al. | | 5,342,357 A | 8/1994 | Nardella |
| 4,827,911 A | 5/1989 | Broadwin et al. | | 5,342,409 A | 8/1994 | Mullett |
| 4,827,927 A | 5/1989 | Newton | | 5,346,406 A | 9/1994 | Hoffman et al. |
| 4,832,024 A | 5/1989 | Boussignac et al. | | 5,346,491 A | 9/1994 | Oertli |
| 4,848,335 A | 7/1989 | Manes | | 5,348,554 A | 9/1994 | Imran et al. |
| 4,848,355 A | 7/1989 | Nakamura et al. | | 5,370,645 A * | 12/1994 | Klicek et al. ............ 606/35 |
| 4,860,745 A | 8/1989 | Farin et al. | | 5,370,672 A | 12/1994 | Fowler et al. |
| 4,862,889 A | 9/1989 | Feucht | | 5,370,675 A | 12/1994 | Edwards et al. |
| 4,880,719 A | 11/1989 | Murofushi et al. | | 5,372,596 A | 12/1994 | Klicek et al. |
| 4,887,199 A | 12/1989 | Whittle | | 5,383,874 A | 1/1995 | Jackson |
| 4,890,610 A | 1/1990 | Kirwan et al. | | 5,383,876 A | 1/1995 | Nardella |
| 4,903,696 A | 2/1990 | Stasz et al. | | 5,383,917 A | 1/1995 | Desai et al. |
| 4,907,589 A | 3/1990 | Cosman | | 5,385,148 A | 1/1995 | Lesh et al. |
| 4,922,210 A | 5/1990 | Flachenecker et al. | | 5,396,062 A | 3/1995 | Eisentraut et al. |
| 4,931,047 A | 6/1990 | Broadwin et al. | | 5,400,267 A | 3/1995 | Denen et al. |
| 4,931,717 A | 6/1990 | Gray et al. | | 5,403,311 A | 4/1995 | Abele et al. |
| 4,938,761 A | 7/1990 | Ensslin | | 5,403,312 A | 4/1995 | Yates et al. |
| 4,942,313 A | 7/1990 | Kinzel | | 5,409,000 A | 4/1995 | Imran |
| 4,959,606 A | 9/1990 | Forge | | 5,409,006 A | 4/1995 | Buchholtz et al. |
| 4,961,047 A | 10/1990 | Carder | | 5,409,485 A | 4/1995 | Suda |
| 4,961,435 A | 10/1990 | Kitagawa et al. | | 5,413,573 A | 5/1995 | Koivukangas |
| 4,966,597 A | 10/1990 | Cosman | | 5,414,238 A | 5/1995 | Steigerwald et al. |
| RE33,420 E | 11/1990 | Sussman | | 5,417,719 A | 5/1995 | Hull et al. |
| 4,969,885 A | 11/1990 | Farin | | 5,422,567 A | 6/1995 | Matsunaga |
| 4,992,719 A | 2/1991 | Harvey | | 5,422,926 A | 6/1995 | Smith et al. |
| 4,993,430 A | 2/1991 | Shimoyama et al. | | 5,423,808 A | 6/1995 | Edwards et al. |
| 4,995,877 A | 2/1991 | Ams et al. | | 5,423,809 A | 6/1995 | Klicek |
| 5,015,227 A | 5/1991 | Broadwin et al. | | 5,423,810 A | 6/1995 | Goble et al. |
| 5,019,176 A | 5/1991 | Brandhorst, Jr. | | 5,423,811 A | 6/1995 | Imran et al. |
| 5,024,668 A | 6/1991 | Peters et al. | | 5,425,704 A | 6/1995 | Sakurai et al. |
| 5,029,588 A | 7/1991 | Yock et al. | | 5,429,596 A | 7/1995 | Arias et al. |
| 5,044,977 A | 9/1991 | Vindigni | | 5,430,434 A | 7/1995 | Lederer et al. |
| 5,067,953 A | 11/1991 | Feucht | | 5,432,459 A | 7/1995 | Thompson |
| 5,075,839 A | 12/1991 | Fisher et al. | | 5,433,739 A | 7/1995 | Sluijter et al. |
| 5,087,257 A | 2/1992 | Farin | | 5,434,398 A | 7/1995 | Goldberg |
| 5,099,840 A | 3/1992 | Goble et al. | | 5,436,566 A | 7/1995 | Thompson |
| 5,103,804 A | 4/1992 | Abele et al. | | 5,438,302 A | 8/1995 | Goble |
| 5,108,389 A | 4/1992 | Cosmescu | | 5,443,463 A | 8/1995 | Stern et al. |
| 5,108,391 A | 4/1992 | Flachenecker | | 5,445,635 A | 8/1995 | Denen et al. |
| 5,119,284 A | 6/1992 | Fisher et al. | | 5,451,224 A | 9/1995 | Goble et al. |
| 5,122,137 A | 6/1992 | Lennox | | 5,452,725 A | 9/1995 | Martenson |
| 5,133,711 A | 7/1992 | Hagen | | 5,454,809 A | 10/1995 | Janssen |
| 5,151,102 A | 9/1992 | Kamiyama et al. | | 5,458,597 A | 10/1995 | Edwards et al. |
| 5,152,762 A | 10/1992 | McElhenney | | 5,462,521 A | 10/1995 | Brucker et al. |
| 5,157,603 A | 10/1992 | Scheller et al. | | 5,472,441 A | 12/1995 | Edwards et al. |
| 5,160,334 A | 11/1992 | Billings et al. | | 5,472,443 A | 12/1995 | Cordis et al. |
| 5,161,893 A | 11/1992 | Shigezawa et al. | | 5,474,464 A | 12/1995 | Drewnicki |
| 5,162,217 A | 11/1992 | Hartman | | 5,478,303 A | 12/1995 | Foley-Nolan et al. |
| 5,167,658 A | 12/1992 | Ensslin | | 5,480,399 A | 1/1996 | Hebborn |
| 5,167,659 A | 12/1992 | Ohtomo et al. | | 5,483,952 A | 1/1996 | Aranyi |
| 5,190,517 A | 3/1993 | Zieve et al. | | 5,490,850 A | 2/1996 | Ellman et al. |
| 5,196,008 A | 3/1993 | Kuenecke | | 5,496,312 A * | 3/1996 | Klicek ............ 606/34 |
| 5,196,009 A | 3/1993 | Kirwan, Jr. | | 5,496,313 A | 3/1996 | Gentelia et al. |
| 5,201,900 A | 4/1993 | Nardella | | 5,496,314 A | 3/1996 | Eggers |
| 5,207,691 A | 5/1993 | Nardella | | 5,500,012 A | 3/1996 | Brucker et al. |
| 5,230,623 A | 7/1993 | Guthrie et al. | | 5,500,616 A | 3/1996 | Ochi |
| 5,233,515 A | 8/1993 | Cosman | | 5,511,993 A | 4/1996 | Yamada et al. |
| 5,234,427 A | 8/1993 | Ohtomo et al. | | 5,514,129 A | 5/1996 | Smith |
| 5,249,121 A | 9/1993 | Baum et al. | | 5,520,684 A | 5/1996 | Imran |
| 5,249,585 A | 10/1993 | Turner et al. | | 5,531,774 A | 7/1996 | Schulman et al. |
| 5,254,117 A | 10/1993 | Rigby et al. | | 5,534,018 A | 7/1996 | Wahlstrand et al. |
| RE34,432 E | 11/1993 | Bertrand | | 5,536,267 A | 7/1996 | Edwards et al. |
| 5,267,994 A | 12/1993 | Gentelia et al. | | 5,540,677 A | 7/1996 | Sinofsky |
| 5,267,997 A | 12/1993 | Farin | | 5,540,681 A | 7/1996 | Strul et al. |
| 5,281,213 A | 1/1994 | Milder et al. | | 5,540,682 A | 7/1996 | Gardner et al. |
| 5,282,840 A | 2/1994 | Hudrlik | | 5,540,683 A | 7/1996 | Ichikawa |
| 5,290,283 A | 3/1994 | Suda | | 5,540,684 A | 7/1996 | Hassler, Jr. |
| 5,295,857 A | 3/1994 | Toly | | 5,540,724 A | 7/1996 | Cox |
| 5,300,068 A | 4/1994 | Rosar et al. | | 5,541,376 A | 7/1996 | Ladtkow et al. |
| 5,300,070 A | 4/1994 | Gentelia | | 5,545,161 A | 8/1996 | Imran |
| 5,304,917 A | 4/1994 | Somerville | | 5,556,396 A | 9/1996 | Cohen et al. |
| 5,318,563 A | 6/1994 | Malis et al. | | 5,558,671 A * | 9/1996 | Yates ............ 606/38 |
| 5,323,778 A | 6/1994 | Kandarpa et al. | | 5,562,720 A | 10/1996 | Stern et al. |
| 5,324,283 A | 6/1994 | Heckele | | 5,569,242 A | 10/1996 | Lax et al. |
| 5,330,518 A | 7/1994 | Neilson et al. | | 5,571,147 A | 11/1996 | Sluijter et al. |
| 5,334,183 A | 8/1994 | Wuchinich | | 5,573,533 A | 11/1996 | Strul |
| 5,334,193 A | 8/1994 | Nardella | | 5,584,830 A | 12/1996 | Ladd et al. |
| 5,341,807 A | 8/1994 | Nardella | | 5,588,432 A | 12/1996 | Crowley |
| 5,342,356 A | 8/1994 | Ellman et al. | | 5,594,836 A | 1/1997 | Ryu et al. |

| | | | | | | |
|---|---|---|---|---|---|---|
| 5,596,466 A | 1/1997 | Ochi | | 5,868,739 A | 2/1999 | Lindenmeier et al. |
| 5,599,344 A | 2/1997 | Paterson | | 5,868,740 A | 2/1999 | LeVeen et al. |
| 5,599,345 A | 2/1997 | Edwards et al. | | 5,871,481 A | 2/1999 | Kannenberg et al. |
| 5,599,348 A | 2/1997 | Gentelia et al. | | 5,891,142 A | 4/1999 | Eggers et al. |
| 5,605,150 A | 2/1997 | Radons et al. | | 5,897,552 A | 4/1999 | Edwards et al. |
| 5,609,560 A | 3/1997 | Ichikawa et al. | | 5,906,614 A | 5/1999 | Stern et al. |
| 5,613,966 A | 3/1997 | Makower et al. | | 5,908,444 A | 6/1999 | Azure |
| 5,613,996 A | 3/1997 | Lindsay | | 5,913,882 A | 6/1999 | King |
| 5,620,481 A | 4/1997 | Desai et al. | | 5,921,982 A | 7/1999 | Lesh et al. |
| 5,625,370 A | 4/1997 | D'Hont | | 5,925,070 A | 7/1999 | King et al. |
| 5,626,575 A | 5/1997 | Crenner | | 5,931,836 A | 8/1999 | Hatta et al. |
| 5,628,745 A | 5/1997 | Bek | | 5,938,690 A | 8/1999 | Law et al. |
| 5,628,771 A | 5/1997 | Mizukawa et al. | | 5,944,553 A | 8/1999 | Yasui et al. |
| 5,643,330 A | 7/1997 | Holsheimer et al. | | 5,948,007 A | 9/1999 | Starkebaum et al. |
| 5,647,869 A | 7/1997 | Goble et al. | | 5,951,545 A | 9/1999 | Schilling |
| 5,647,871 A | 7/1997 | Levine et al. | | 5,951,546 A | 9/1999 | Lorentzen |
| 5,651,780 A | 7/1997 | Jackson et al. | | 5,954,686 A | 9/1999 | Garito et al. |
| 5,658,322 A | 8/1997 | Fleming | | 5,954,717 A | 9/1999 | Behl et al. |
| 5,660,567 A | 8/1997 | Nierlich et al. | | 5,954,719 A | 9/1999 | Chen et al. |
| 5,664,953 A | 9/1997 | Reylek | | 5,957,961 A | 9/1999 | Maguire et al. |
| 5,674,217 A | 10/1997 | Wahlstrom et al. | | 5,959,253 A | 9/1999 | Shinchi |
| 5,678,568 A | 10/1997 | Uchikubo et al. | | 5,961,344 A | 10/1999 | Rosales et al. |
| 5,681,307 A | 10/1997 | McMahan | | 5,964,746 A | 10/1999 | McCary |
| 5,685,840 A | 11/1997 | Schechter et al. | | 5,971,980 A | 10/1999 | Sherman |
| 5,688,267 A | 11/1997 | Panescu et al. | | 5,971,981 A | 10/1999 | Hill et al. |
| 5,690,692 A | 11/1997 | Fleming | | 5,976,128 A | 11/1999 | Schilling et al. |
| 5,693,042 A | 12/1997 | Boiarski et al. | | 5,983,141 A | 11/1999 | Sluijter et al. |
| 5,693,078 A | 12/1997 | Desai et al. | | 6,007,532 A | 12/1999 | Netherly |
| 5,694,304 A | 12/1997 | Telefus et al. | | 6,010,499 A | 1/2000 | Cobb |
| 5,695,494 A | 12/1997 | Becker | | 6,013,074 A | 1/2000 | Taylor |
| 5,696,351 A | 12/1997 | Benn et al. | | 6,014,581 A | 1/2000 | Whayne et al. |
| 5,696,441 A | 12/1997 | Mak et al. | | 6,017,338 A | 1/2000 | Brucker et al. |
| 5,697,925 A | 12/1997 | Taylor | | 6,022,346 A | 2/2000 | Panescu et al. |
| 5,697,927 A | 12/1997 | Imran et al. | | 6,022,347 A | 2/2000 | Lindenmeier et al. |
| 5,702,386 A | 12/1997 | Stern et al. | | 6,033,399 A | 3/2000 | Gines |
| 5,702,429 A | 12/1997 | King | | 6,039,731 A | 3/2000 | Taylor et al. |
| 5,707,369 A | 1/1998 | Vaitekunas et al. | | 6,039,732 A | 3/2000 | Ichikawa et al. |
| 5,712,772 A | 1/1998 | Telefus et al. | | 6,041,260 A | 3/2000 | Stern et al. |
| 5,713,896 A | 2/1998 | Nardella | | 6,044,283 A | 3/2000 | Fein et al. |
| 5,718,246 A | 2/1998 | Vona | | 6,053,910 A | 4/2000 | Fleenor |
| 5,720,742 A | 2/1998 | Zacharias | | 6,053,912 A | 4/2000 | Panescu et al. |
| 5,720,744 A | 2/1998 | Eggleston et al. | | 6,055,458 A | 4/2000 | Cochran et al. |
| 5,722,975 A | 3/1998 | Edwards et al. | | 6,056,745 A | 5/2000 | Panescu et al. |
| 5,729,448 A | 3/1998 | Haynie et al. | | 6,056,746 A | 5/2000 | Goble et al. |
| 5,733,281 A | 3/1998 | Nardella | | 6,059,781 A | 5/2000 | Yamanashi et al. |
| 5,735,846 A | 4/1998 | Panescu et al. | | 6,063,075 A | 5/2000 | Mihori |
| 5,738,683 A | 4/1998 | Osypka | | 6,063,078 A | 5/2000 | Wittkampf |
| 5,743,900 A | 4/1998 | Hara | | 6,066,137 A | 5/2000 | Greep |
| 5,743,903 A | 4/1998 | Stern et al. | | 6,068,627 A | 5/2000 | Orszulak et al. |
| 5,749,869 A | 5/1998 | Lindenmeier et al. | | 6,074,089 A | 6/2000 | Hollander et al. |
| 5,749,871 A | 5/1998 | Hood et al. | | 6,074,386 A | 6/2000 | Goble et al. |
| 5,755,715 A * | 5/1998 | Stern et al. ............ 606/31 | | 6,074,388 A | 6/2000 | Tockweiler et al. |
| 5,766,153 A | 6/1998 | Eggers et al. | | 6,080,149 A | 6/2000 | Huang et al. |
| 5,766,165 A | 6/1998 | Gentelia et al. | | 6,088,614 A | 7/2000 | Swanson |
| 5,769,847 A * | 6/1998 | Panescu et al. ............ 606/42 | | 6,093,186 A | 7/2000 | Goble |
| 5,772,659 A | 6/1998 | Becker et al. | | 6,102,497 A | 8/2000 | Ehr et al. |
| 5,788,688 A | 8/1998 | Bauer et al. | | 6,102,907 A | 8/2000 | Smethers et al. |
| 5,792,138 A | 8/1998 | Shipp | | RE36,871 E | 9/2000 | Epstein |
| 5,797,802 A | 8/1998 | Nowak | | 6,113,591 A | 9/2000 | Whayne et al. |
| 5,797,902 A | 8/1998 | Netherly | | 6,113,592 A | 9/2000 | Taylor |
| 5,807,253 A | 9/1998 | Dumoulin et al. | | 6,113,593 A | 9/2000 | Tu et al. |
| 5,810,804 A | 9/1998 | Gough et al. | | 6,113,596 A | 9/2000 | Hooven |
| 5,814,092 A | 9/1998 | King | | 6,123,701 A | 9/2000 | Nezhat |
| 5,817,091 A | 10/1998 | Nardella et al. | | 6,123,702 A * | 9/2000 | Swanson et al. ............ 606/34 |
| 5,817,093 A | 10/1998 | Williamson, IV et al. | | 6,132,429 A | 10/2000 | Baker |
| 5,820,568 A | 10/1998 | Willis | | 6,142,992 A | 11/2000 | Cheng et al. |
| 5,827,271 A | 10/1998 | Buysse et al. | | 6,155,975 A | 12/2000 | Urich et al. |
| 5,830,212 A | 11/1998 | Cartmell | | 6,162,184 A | 12/2000 | Swanson et al. |
| 5,836,909 A | 11/1998 | Cosmescu | | 6,162,217 A | 12/2000 | Kannenberg et al. |
| 5,836,943 A | 11/1998 | Miller, III | | 6,165,169 A | 12/2000 | Panescu et al. |
| 5,836,990 A | 11/1998 | Li | | 6,171,304 B1 | 1/2001 | Netherly et al. |
| 5,843,019 A | 12/1998 | Eggers et al. | | 6,183,468 B1 | 2/2001 | Swanson et al. |
| 5,843,075 A | 12/1998 | Taylor | | 6,186,147 B1 | 2/2001 | Cobb |
| 5,846,236 A | 12/1998 | Lindenmeier et al. | | 6,188,211 B1 | 2/2001 | Rincon-Mora et al. |
| 5,849,010 A | 12/1998 | Wurzer et al. | | 6,193,713 B1 | 2/2001 | Geistert et al. |
| 5,853,409 A | 12/1998 | Swanson et al. | | 6,197,023 B1 | 3/2001 | Muntermann |
| 5,860,832 A | 1/1999 | Wayt et al. | | 6,203,541 B1 | 3/2001 | Keppel |
| 5,865,788 A | 2/1999 | Edwards et al. | | 6,210,403 B1 | 4/2001 | Klicek |
| 5,868,737 A | 2/1999 | Taylor et al. | | 6,216,704 B1 | 4/2001 | Ingle et al. |

| Patent | Date | Name |
|---|---|---|
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 * | 6/2002 | Buysse et al. .................. 606/34 |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 * | 6/2002 | Hoey et al. ....................... 606/34 |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside et al. |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,573,248 B2 | 6/2003 | Ramasamy et al. |
| 6,575,969 B1 * | 6/2003 | Rittman et al. .................. 606/41 |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |

| | | | | | | |
|---|---|---|---|---|---|---|
| 6,860,881 B2 | 3/2005 | Sturm | 7,255,694 B2 | 8/2007 | Keppel | |
| 6,864,686 B2 | 3/2005 | Novak | 7,258,688 B1 | 8/2007 | Shah et al. | |
| 6,875,210 B2 | 4/2005 | Refior | 7,282,048 B2 | 10/2007 | Goble et al. | |
| 6,890,331 B2 | 5/2005 | Kristensen | 7,282,049 B2 | 10/2007 | Orszulak et al. | |
| 6,893,435 B2 | 5/2005 | Goble | 7,285,117 B2 | 10/2007 | Krueger et al. | |
| 6,899,538 B2 | 5/2005 | Matoba | 7,294,127 B2 | 11/2007 | Leung et al. | |
| 6,923,804 B2 | 8/2005 | Eggers et al. | 7,300,435 B2 | 11/2007 | Wham et al. | |
| 6,929,641 B2 | 8/2005 | Goble et al. | 7,300,437 B2 | 11/2007 | Pozzato | |
| 6,936,047 B2 | 8/2005 | Nasab et al. | 7,303,557 B2 | 12/2007 | Wham et al. | |
| 6,939,344 B2 | 9/2005 | Kreindel | 7,305,311 B2 | 12/2007 | Van Zyl | |
| 6,939,346 B2 | 9/2005 | Kannenberg et al. | 7,317,954 B2 | 1/2008 | McGreevy | |
| 6,939,347 B2 | 9/2005 | Thompson | 7,317,955 B2 | 1/2008 | McGreevy | |
| 6,942,660 B2 | 9/2005 | Pantera et al. | 7,324,357 B2 | 1/2008 | Miura et al. | |
| 6,948,503 B2 | 9/2005 | Refior et al. | 7,333,859 B2 | 2/2008 | Rinaldi et al. | |
| 6,958,064 B2 | 10/2005 | Rioux et al. | 7,341,586 B2 | 3/2008 | Daniel et al. | |
| 6,962,587 B2 | 11/2005 | Johnson et al. | 7,344,532 B2 | 3/2008 | Goble et al. | |
| 6,966,907 B2 | 11/2005 | Goble | 7,353,068 B2 | 4/2008 | Tanaka et al. | |
| 6,974,453 B2 | 12/2005 | Woloszko et al. | 7,354,436 B2 | 4/2008 | Rioux et al. | |
| 6,974,463 B2 | 12/2005 | Magers et al. | 7,357,800 B2 | 4/2008 | Swanson | |
| 6,977,495 B2 | 12/2005 | Donofrio | 7,364,577 B2 | 4/2008 | Wham et al. | |
| 6,984,231 B2 | 1/2006 | Goble et al. | 7,364,578 B2 | 4/2008 | Francischelli et al. | |
| 6,989,010 B2 | 1/2006 | Francischelli et al. | 7,364,972 B2 | 4/2008 | Ono et al. | |
| 6,994,704 B2 | 2/2006 | Qin et al. | 7,367,972 B2 | 5/2008 | Francischelli et al. | |
| 6,994,707 B2 | 2/2006 | Ellman et al. | RE40,388 E | 6/2008 | Gines | |
| 7,001,379 B2 | 2/2006 | Behl et al. | 7,396,336 B2 | 7/2008 | Orszulak et al. | |
| 7,001,381 B2 | 2/2006 | Harano et al. | 7,402,754 B2 | 7/2008 | Kirwan, Jr. et al. | |
| 7,004,174 B2 | 2/2006 | Eggers et al. | D574,323 S | 8/2008 | Waaler | |
| 7,008,369 B2 | 3/2006 | Cuppen | 7,407,502 B2 | 8/2008 | Strul et al. | |
| 7,008,417 B2 | 3/2006 | Eick | 7,416,437 B2 | 8/2008 | Sartor et al. | |
| 7,008,421 B2 | 3/2006 | Daniel et al. | 7,416,549 B2 | 8/2008 | Young et al. | |
| 7,025,764 B2 | 4/2006 | Paton et al. | 7,422,582 B2 | 9/2008 | Malackowski et al. | |
| 7,033,351 B2 | 4/2006 | Howell | 7,422,586 B2 | 9/2008 | Morris et al. | |
| 7,041,096 B2 | 5/2006 | Malis et al. | 7,425,835 B2 | 9/2008 | Eisele | |
| 7,044,948 B2 | 5/2006 | Keppel | 7,465,302 B2 | 12/2008 | Odell et al. | |
| 7,044,949 B2 | 5/2006 | Orszulak et al. | 7,470,272 B2 | 12/2008 | Mulier et al. | |
| 7,060,063 B2 | 6/2006 | Marion et al. | 7,479,140 B2 | 1/2009 | Ellman et al. | |
| 7,062,331 B2 | 6/2006 | Zarinetchi et al. | 7,491,199 B2 | 2/2009 | Goble | |
| 7,063,692 B2 | 6/2006 | Sakurai et al. | 7,491,201 B2 | 2/2009 | Shields et al. | |
| 7,066,933 B2 | 6/2006 | Hagg | 7,513,896 B2 | 4/2009 | Orszulak | |
| 7,074,217 B2 | 7/2006 | Strul et al. | 7,525,398 B2 | 4/2009 | Nishimura et al. | |
| 7,083,618 B2 | 8/2006 | Couture et al. | 2001/0014804 A1 | 8/2001 | Goble et al. | |
| 7,094,231 B1 | 8/2006 | Ellman et al. | 2001/0029315 A1 | 10/2001 | Sakurai et al. | |
| RE39,358 E | 10/2006 | Goble | 2001/0031962 A1 | 10/2001 | Eggleston | |
| 7,115,121 B2 | 10/2006 | Novak | 2002/0035363 A1 | 3/2002 | Edwards et al. | |
| 7,115,124 B1 | 10/2006 | Xiao | 2002/0035364 A1 | 3/2002 | Schoenman et al. | |
| 7,118,564 B2 | 10/2006 | Ritchie et al. | 2002/0052599 A1 | 5/2002 | Goble | |
| 7,122,031 B2 | 10/2006 | Edwards et al. | 2002/0068932 A1 | 6/2002 | Edwards | |
| 7,131,445 B2 | 11/2006 | Amoah | 2002/0107517 A1 | 8/2002 | Witt et al. | |
| 7,131,860 B2 | 11/2006 | Sartor et al. | 2002/0111624 A1 | 8/2002 | Witt et al. | |
| 7,137,980 B2 | 11/2006 | Buysse et al. | 2002/0151889 A1 | 10/2002 | Swanson et al. | |
| 7,146,210 B2 | 12/2006 | Palti | 2002/0193787 A1 | 12/2002 | Qin | |
| 7,147,638 B2 | 12/2006 | Chapman et al. | 2003/0004510 A1 | 1/2003 | Wham et al. | |
| 7,151,964 B2 | 12/2006 | Desai et al. | 2003/0060818 A1 | 3/2003 | Kannenberg | |
| 7,153,300 B2 | 12/2006 | Goble | 2003/0078572 A1 | 4/2003 | Pearson et al. | |
| 7,156,844 B2 | 1/2007 | Reschke et al. | 2003/0139741 A1 | 7/2003 | Goble et al. | |
| 7,156,846 B2 | 1/2007 | Dycus et al. | 2003/0153908 A1 | 8/2003 | Goble | |
| 7,160,293 B2 | 1/2007 | Sturm et al. | 2003/0163123 A1 | 8/2003 | Goble | |
| 7,163,536 B2 | 1/2007 | Godara | 2003/0163124 A1 | 8/2003 | Goble | |
| 7,169,144 B2 | 1/2007 | Hoey et al. | 2003/0171745 A1 | 9/2003 | Francischelli | |
| 7,172,591 B2 | 2/2007 | Harano et al. | 2003/0181898 A1 | 9/2003 | Bowers | |
| 7,175,618 B2 | 2/2007 | Dabney et al. | 2003/0199863 A1 | 10/2003 | Swanson | |
| 7,175,621 B2 | 2/2007 | Heim et al. | 2003/0225401 A1 | 12/2003 | Eggers et al. | |
| 7,192,427 B2 | 3/2007 | Chapelon et al. | 2004/0002745 A1 | 1/2004 | Fleming | |
| 7,195,627 B2 | 3/2007 | Amoah et al. | 2004/0015159 A1 | 1/2004 | Slater et al. | |
| 7,203,556 B2 | 4/2007 | Daners | 2004/0015163 A1* | 1/2004 | Buysse et al. | 606/34 |
| 7,211,081 B2 | 5/2007 | Goble | 2004/0015216 A1 | 1/2004 | DeSisto | |
| 7,214,224 B2 | 5/2007 | Goble | 2004/0019347 A1 | 1/2004 | Sakurai | |
| 7,217,269 B2 | 5/2007 | El-Galley et al. | 2004/0024395 A1 | 2/2004 | Ellman | |
| 7,220,260 B2 | 5/2007 | Fleming et al. | 2004/0030328 A1 | 2/2004 | Eggers | |
| 7,223,264 B2 | 5/2007 | Daniel et al. | 2004/0030330 A1 | 2/2004 | Brassell et al. | |
| 7,226,447 B2 | 6/2007 | Uchida et al. | 2004/0044339 A1 | 3/2004 | Beller | |
| 7,229,469 B1 | 6/2007 | Witzel et al. | 2004/0049179 A1 | 3/2004 | Francischelli | |
| 7,232,437 B2 | 6/2007 | Berman et al. | 2004/0054365 A1 | 3/2004 | Goble | |
| 7,238,181 B2 | 7/2007 | Daners et al. | 2004/0059323 A1 | 3/2004 | Sturm et al. | |
| 7,238,183 B2 | 7/2007 | Kreindel | 2004/0068304 A1 | 4/2004 | Paton | |
| 7,244,255 B2 | 7/2007 | Daners et al. | 2004/0082946 A1 | 4/2004 | Malis | |
| 7,247,155 B2 | 7/2007 | Hoey et al. | 2004/0095100 A1 | 5/2004 | Thompson | |
| 7,250,048 B2 | 7/2007 | Francischelli et al. | 2004/0097912 A1 | 5/2004 | Gonnering | |
| 7,250,746 B2 | 7/2007 | Oswald et al. | 2004/0097914 A1 | 5/2004 | Pantera | |

| | | | | | |
|---|---|---|---|---|---|
| 2004/0097915 A1 | 5/2004 | Refior | DE | 2455174 | 5/1975 |
| 2004/0116919 A1 | 6/2004 | Heim | DE | 2407559 | 8/1975 |
| 2004/0133189 A1 | 7/2004 | Sakurai | DE | 2602517 | 7/1976 |
| 2004/0138653 A1 | 7/2004 | Dabney et al. | DE | 2504280 | 8/1976 |
| 2004/0138654 A1 | 7/2004 | Goble | DE | 2540968 | 3/1977 |
| 2004/0143263 A1 | 7/2004 | Schechter et al. | DE | 2820908 | 11/1978 |
| 2004/0147918 A1 | 7/2004 | Keppel | DE | 2803275 | 8/1979 |
| 2004/0167508 A1 | 8/2004 | Wham et al. | DE | 2823291 | 11/1979 |
| 2004/0172016 A1 | 9/2004 | Bek | DE | 2946728 | 5/1981 |
| 2004/0193148 A1 | 9/2004 | Wham et al. | DE | 3143421 | 5/1982 |
| 2004/0230189 A1 | 11/2004 | Keppel | DE | 3045996 | 7/1982 |
| 2004/0243120 A1 | 12/2004 | Orszulak et al. | DE | 3120102 | 12/1982 |
| 2004/0260279 A1 | 12/2004 | Goble | DE | 3510586 | 10/1986 |
| 2005/0004564 A1 | 1/2005 | Wham | DE | 3604823 | 8/1987 |
| 2005/0004569 A1 | 1/2005 | Witt et al. | DE | 390937 | 4/1989 |
| 2005/0004634 A1 | 1/2005 | Ricart et al. | DE | 3904558 | 8/1990 |
| 2005/0021020 A1 | 1/2005 | Blaha et al. | DE | 3942998 | 7/1991 |
| 2005/0021022 A1 | 1/2005 | Sturm et al. | DE | 4339049 A1 | 5/1995 |
| 2005/0101949 A1 | 5/2005 | Harano et al. | DE | 19717411 | 11/1998 |
| 2005/0101951 A1 | 5/2005 | Wham | DE | 19848540 A1 | 5/2000 |
| 2005/0109111 A1 | 5/2005 | Manlove et al. | EP | 246350 | 11/1987 |
| 2005/0113818 A1 | 5/2005 | Sartor | EP | 310431 | 4/1989 |
| 2005/0113819 A1 | 5/2005 | Wham | EP | 325456 | 7/1989 |
| 2005/0149151 A1 | 7/2005 | Orszulak | EP | 336742 | 10/1989 |
| 2005/0182398 A1 | 8/2005 | Paterson | EP | 390937 | 10/1990 |
| 2005/0197659 A1 | 9/2005 | Bahney | EP | 556705 | 8/1993 |
| 2005/0203504 A1 | 9/2005 | Wham et al. | EP | 0569130 A1 | 11/1993 |
| 2006/0025760 A1 | 2/2006 | Podhajsky | EP | 608609 | 8/1994 |
| 2006/0079871 A1 | 4/2006 | Plaven et al. | EP | 0694291 | 1/1996 |
| 2006/0111711 A1 | 5/2006 | Goble | EP | 836868 | 4/1998 |
| 2006/0161148 A1 | 7/2006 | Behnke | EP | 878169 | 11/1998 |
| 2006/0178664 A1 | 8/2006 | Keppel | EP | 1051948 | 11/2000 |
| 2006/0224152 A1 | 10/2006 | Behnke et al. | EP | 1053720 | 11/2000 |
| 2006/0281360 A1 | 12/2006 | Sartor et al. | EP | 1151725 | 11/2001 |
| 2006/0291178 A1 | 12/2006 | Shih | EP | 1293171 | 3/2003 |
| 2007/0038209 A1 | 2/2007 | Buysse et al. | EP | 1472984 | 11/2004 |
| 2007/0093800 A1 | 4/2007 | Wham et al. | EP | 1495712 | 1/2005 |
| 2007/0093801 A1 | 4/2007 | Behnke | EP | 1500378 | 1/2005 |
| 2007/0135812 A1 | 6/2007 | Sartor | EP | 1535581 | 6/2005 |
| 2007/0173802 A1 | 7/2007 | Keppel | EP | 1609430 | 12/2005 |
| 2007/0173803 A1 | 7/2007 | Wham et al. | EP | 1707144 | 3/2006 |
| 2007/0173804 A1 | 7/2007 | Wham et al. | EP | 1645235 | 4/2006 |
| 2007/0173805 A1 | 7/2007 | Weinberg et al. | EP | 0880220 B1 | 6/2006 |
| 2007/0173806 A1 | 7/2007 | Orszulak et al. | EP | 1707143 | 10/2006 |
| 2007/0173810 A1 | 7/2007 | Orszulak | EP | 1744354 | 1/2007 |
| 2007/0173813 A1 | 7/2007 | Odom | EP | 1810628 | 7/2007 |
| 2007/0208339 A1 | 9/2007 | Arts et al. | EP | 1810630 | 7/2007 |
| 2007/0225698 A1 | 9/2007 | Orszulak et al. | EP | 1810633 | 7/2007 |
| 2007/0250052 A1 | 10/2007 | Wham | EP | 1854423 | 11/2007 |
| 2007/0265612 A1 | 11/2007 | Behnke et al. | FR | 1275415 | 10/1961 |
| 2007/0282320 A1 | 12/2007 | Buysse et al. | FR | 1347865 | 11/1963 |
| 2008/0015563 A1 | 1/2008 | Hoey et al. | FR | 2313708 | 12/1976 |
| 2008/0015564 A1 | 1/2008 | Wham et al. | FR | 2364461 | 7/1978 |
| 2008/0039831 A1 | 2/2008 | Odom et al. | FR | 2502935 | 10/1982 |
| 2008/0039836 A1 | 2/2008 | Odom et al. | FR | 2517953 | 6/1983 |
| 2008/0082094 A1 | 4/2008 | McPherson et al. | FR | 2573301 | 5/1986 |
| 2008/0125767 A1 | 5/2008 | Blaha | GB | 607850 | 9/1948 |
| 2008/0177199 A1 | 7/2008 | Podhajsky | GB | 702510 | 1/1954 |
| 2008/0248685 A1 | 10/2008 | Sartor et al. | GB | 855459 | 11/1960 |
| 2008/0281315 A1 | 11/2008 | Gines | GB | 902775 | 8/1962 |
| 2008/0281316 A1 | 11/2008 | Carlton et al. | GB | 2164473 | 3/1986 |
| 2008/0287791 A1 | 11/2008 | Orszulak et al. | GB | 2214430 | 9/1989 |
| 2008/0287838 A1 | 11/2008 | Orszulak et al. | GB | 2358934 A | 8/2001 |
| 2009/0018536 A1 | 1/2009 | Behnke | SU | 166452 | 1/1965 |
| 2009/0024120 A1 | 1/2009 | Sartor | SU | 727201 | 4/1980 |
| 2009/0036883 A1 | 2/2009 | Behnke | WO | WO92/06642 | 4/1992 |
| 2009/0069801 A1 | 3/2009 | Jensen et al. | WO | WO93/24066 | 12/1993 |
| 2009/0082765 A1 | 3/2009 | Collins et al. | WO | WO94/24949 | 11/1994 |
| 2009/0157071 A1 | 6/2009 | Wham et al. | WO | WO94/28809 | 12/1994 |
| 2009/0157072 A1 | 6/2009 | Wham et al. | WO | WO95/09577 | 4/1995 |
| 2009/0157073 A1 | 6/2009 | Orszulak | WO | WO95/19148 | 7/1995 |
| 2009/0157075 A1 | 6/2009 | Wham et al. | WO | WO95/25471 | 9/1995 |
| | | | WO | WO96/02180 | 2/1996 |
| | FOREIGN PATENT DOCUMENTS | | WO | WO96/04860 | 2/1996 |
| DE | 1099658 | 2/1961 | WO | WO96/08794 | 3/1996 |
| DE | 1139927 | 11/1962 | WO | WO96/18349 | 6/1996 |
| DE | 1149832 | 6/1963 | WO | WO96/29946 | 10/1996 |
| DE | 1439302 | 1/1969 | WO | WO96/39086 | 12/1996 |
| DE | 2439587 | 2/1975 | WO | WO96/39914 | 12/1996 |

| | | |
|---|---|---|
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060849 | 7/2005 |
| WO | WO2006/050888 | 5/2006 |
| WO | WO2006/105121 | 10/2006 |

OTHER PUBLICATIONS

International Search Report EP 07010673.7 dated Sep. 24, 2007.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2;(Mar. 2005); 160-164.
Medtrex Brochure "The O.R. Pro 300" 1 p. Sep. 1998.
Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
Bergdahl et al. "Studies on Coagulation and the Development of an Automatic Computerized Bipolar Coagulator" J.Neurosurg, vol. 75, Jul. 1991, pp. 148-151.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing. 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic computerized Bipolar Coagulator" Journal of Neurosurgery 75:1. (Jul. 1991) pp. 148-151.
Chicharo et al. "A Sliding Goertzel Algorith" Aug. 1998, pp. 283-297 Signal Processing. Elsevier Science Publishers B.V. Amsterdam. NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedance" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Medtrex Brochure "The O.R. Pro 300" 1p. Sep. 1998.
Valleylab Brochure "Valleylab Electroshield Monitoring System" 2pp. Nov. 1995.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
US 6,878,148, 04/2005, Goble et al. (withdrawn)

* cited by examiner

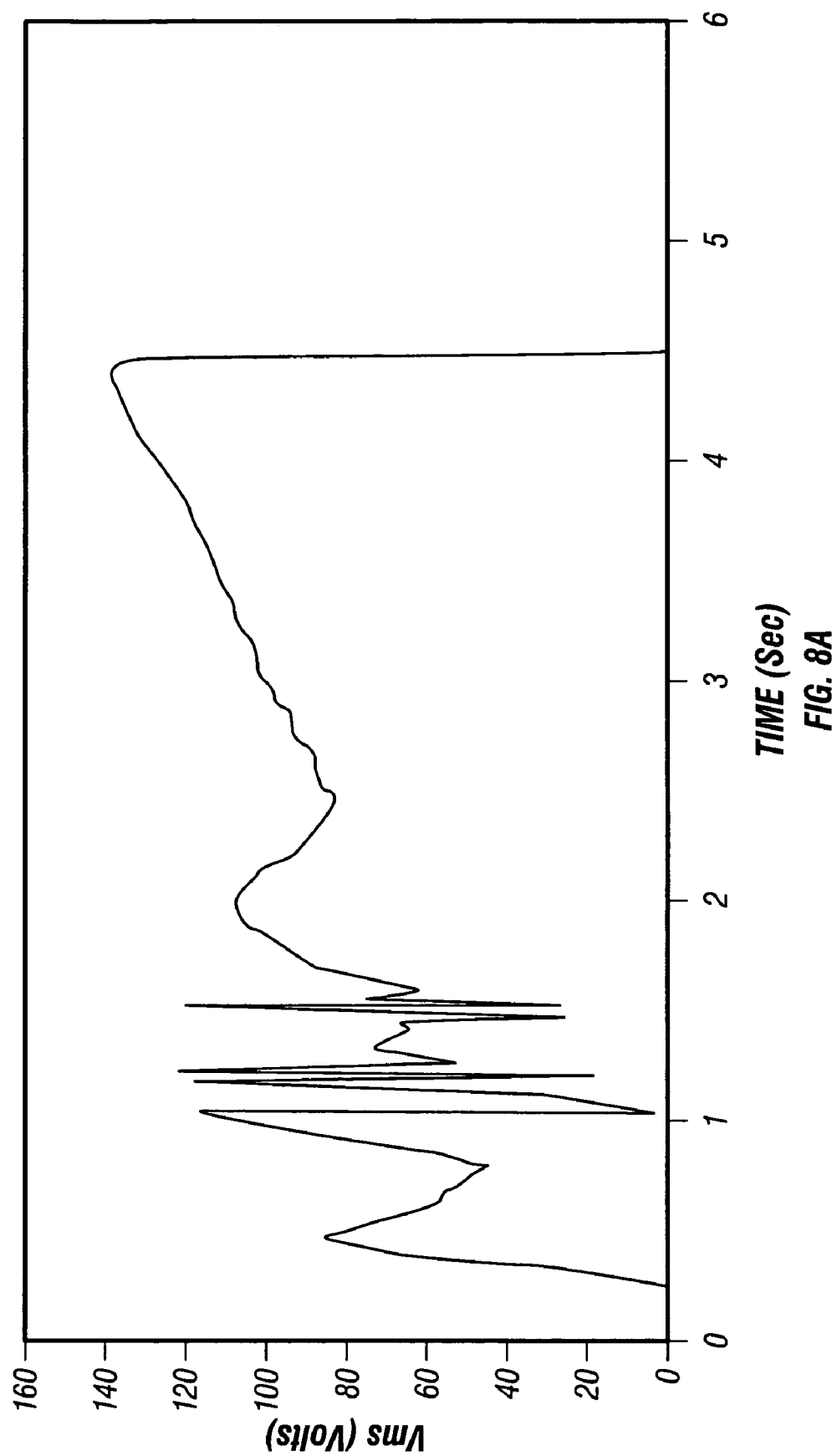

METHOD AND SYSTEM FOR CONTROLLING OUTPUT OF RF MEDICAL GENERATOR

CROSS-REFERENCE TO RELATED APPLICATIONS

This application is a continuation-in-part of U.S. application Ser. No. 10/427,832, now U.S. Pat. No. 7,137,980, filed on May 1, 2003, by Buysse et al., entitled "METHOD AND SYSTEM FOR CONTROLLING OUTPUT OF RF MEDICAL GENERATOR", which is a continuation-in-part of U.S. application Ser. No. 10/073,761, now U.S. Pat. No. 6,796,981, filed Feb. 11, 2002, by Wham et al., entitled "VESSEL SEALING SYSTEM", which is a continuation-in-part of U.S. application Ser. No. 09/408,944, now U.S. Pat. No. 6,398,779, filed on Sep. 30, 1999 by Buysse et al., entitled "VESSEL SEALING SYSTEM", which claims the benefit of the priority date for provisional application No. 60/105,417, filed on Oct. 23, 1998, each of which are incorporated herein in their entirety. This application also claims priority to a provisional application entitled "METHOD AND SYSTEM FOR CONTROLLING OUTPUT OF RF MEDICAL GENERATOR" filed in the United States Patent and Trademark Office on Jan. 27, 2004 and assigned Ser. No. 60/539,804, the contents of which are hereby incorporated by reference.

BACKGROUND

The present disclosure is directed to control systems for electrosurgical generators, and, more particularly, the present disclosure relates to a closed loop control system which continually monitors and drives an electrical impedance response along an ideal curve to optimize tissue sealing irrespective of tissue type or tissue thickness.

TECHNICAL FIELD

Electrosurgical generators are employed by surgeons in conjunction with an electrosurgical instrument or tool to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain, skin, liver and intestine. A surgeon can cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electrodiathermy"). The term "coagulation" is defined as a process of desiccating tissue wherein the tissue cells are ruptured and dried. "Vessel sealing" is defined as the process of liquefying the collagen and elastin in the tissue so that it reforms into a fused mass with significantly-reduced demarcation between the opposing tissue structures (e.g., opposing walls of the lumen). The term "tissue fusion" which is often used synonymously with vessel sealing is defined as the permanent and irreversible interlocking of structural proteins in soft tissue structures in a fashion as to prevent the flow of bodily fluids. Coagulation of small vessels is usually sufficient to permanently close them. Larger vessels or tissue need to be sealed or fused to assure permanent closure.

To achieve one of the above desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

Moreover, it has been determined that to ideally fuse tissue, a delicate balance must be sustained during the fusion process between heating to denature proteins and vaporize fluids and overheating tissue resulting in irreversible tissue damage or overactive immune response. In other words, uncontrolled impedance causes overheating of tissue which leads to a dry, weak seal which is subject to rupture and collateral tissue damage or over-reactive healing response. Under heating of tissue results in an insufficient impedance rise which leads to incomplete and ineffective tissue response (e.g., lack of fusion) which is also subject to fluid leakage and may lead to insufficient healing or possible scarring.

It is known that measuring the electrical impedance and change thereof across the tissue at the surgical site provides a good indication of the state of desiccation or drying of the tissue, e.g., as the tissue dries or looses moisture, the impedance across the tissue or change ion impedance rises. This observation has been utilized in some electrosurgical generators to regulate the electrosurgical power based on a measurement of tissue impedance. For example, commonly owned U.S. Pat. No. 6,210,403 relates to a system and method for automatically measuring the tissue impedance and altering the output of the electrosurgical generator based on the measured impedance across the tissue. The entire contents of this patent are hereby incorporated by reference herein. This patent does not disclose forcing the measured impedance response along an ideal fusion curve to optimize vessel fusion or sealing irrespective of tissue type or tissue thickness.

It has been determined that the particular waveform of electrosurgical energy can be tailored to enhance a desired surgical effect, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. To effectively and consistently seal vessels or tissue, a pulse-like waveform is preferred. Energy may be supplied in a continuous fashion to seal vessels in tissue if the energy input/output is responsive to tissue hydration/volume and composition through feedback control. Delivery of the electrosurgical energy in pulses allows the tissue to cool down and also allows some moisture to return to the tissue between pulses which are both known to enhance the fusion/sealing process.

It is further known to clamp or clip excess voltage output from the electrosurgical generator by the use of avalanche devices, such as diodes, zener diodes and transorbs, resulting in absorption and dissipation of excess energy in the form of heat.

Commonly owned U.S. Pat. No. 6,398,779, which is incorporated by reference herein in its entirety, discloses a sensor which measures the initial tissue impedance with a calibrating pulse which, in turn, sets various electrical parameters based on a look-up table stored in a computer database. The transient pulse width associated with each pulse measured during activation is used to set the duty cycle and amplitude of the next pulse. Generation of electrosurgical power is automatically terminated based on a predetermined value of the tissue impedance across the tissue.

There exists a need to develop an electrosurgical generator having improved control circuitry and/or processing for providing continuous control of various electrical parameters (e.g., frequency and intensity, voltage, current, power, wave parameters, etc.) of the electrosurgical energy output by the electrosurgical generator based upon sensing information obtained from the surgical site relating to tissue impedance, changes in tissue impedance, tissue temperature, changes in tissue temperature, surgical intent (e.g., cutting, coagulating, sealing), tissue type, leakage current, applied voltage, applied current, tissue hydration levels, tissue compliance, and/or tissue optic transmission. Preferably, the generator continually monitors the impedance across the tissue and delivers an appropriate amount of electrosurgical energy to drive the tissue fusion process along an ideal fusion curve to optimize the tissue seal and reduce the likelihood of fluid leakage.

SUMMARY

The present disclosure relates to a system for controlling an electrosurgical generator generating electrosurgical energy which is delivered to a patient for performing an electrosurgical procedure for sealing tissue. The system includes a control module executable on at least one processor for receiving sensed data corresponding to at least one physical or electrical property related to delivery of the electrosurgical energy, wherein the sensed data is sensed by at least one sensor. The control module processes at least a portion of said received sensed data and controls the electrosurgical generator including generating at least one corresponding control signal in accordance with said processed sensed data for regulating electrosurgical energy output from said electrosurgical generator. The controlling the electrosurgical generator further includes regulating at least one control variable, a respective control variable of the at least one control variable corresponding to sensed data corresponding to a property of the at least one physical or electrical property to follow at least one mapping for optimizing the tissue sealing.

In another embodiment of the disclosure a control system associated with an electrosurgical generator generating electrosurgical energy is provided The electrosurgical energy is delivered to a patient for performing an electrosurgical procedure for sealing tissue. The system includes a control module executable on at least one processor for controlling an electrosurgical instrument delivering electrosurgical energy generated by the electrosurgical generator, wherein the electrosurgical instrument includes an array of electrodes configured as micro-sealing pads. The electrosurgical energy output by the electrosurgical generator flows through a respective micro-sealing pad for applying electrosurgical energy to a limited area of tissue for sealing the area of tissue for forming a micro-seal, wherein at least one area of tissue in between respective micro-sealing pads of the array of micro-sealing pads remains substantially viable for creating an intermittent pattern of individual micro-seals across tissue treated by the electrosurgical instrument. The control module further controls delivery of electrosurgical energy to individual micro-sealing pads of the array of micro-sealing pads for at least one of selecting at least one micro-sealing pad to receive electrosurgical energy and providing electrosurgical energy having a first electrical potential to a first selected at least one micro-sealing pad and a second electrical potential to a second selected at least one micro-sealing pad.

In still another embodiment of the invention a method is provided for controlling an electrosurgical generator generating electrosurgical energy which is delivered to a patient for performing an electrosurgical procedure for sealing tissue. The method includes the steps of continually sensing at least one physical or electrical property proximate the surgical site; generating sensed data corresponding to the sensing; processing at least a portion of said sensed data; and controlling the electrosurgical generator. The controlling the electrosurgical generator includes the steps of generating at least one corresponding control signal in accordance with said processed sensed data for regulating electrosurgical energy output from said electrosurgical generator; and regulating at least one control variable to follow at least one mapping for optimizing the tissue sealing. A respective control variable of the at least one control variable corresponds to sensed data which corresponds to a property of the at least one physical or electrical property.

Preferably, the control module is executable on a processor which receives signals from the sensor and processes the signals utilizing a computer algorithm and/or a mapping and generates one or more control signals relating thereto. The control signal(s) is then communicated to the electrosurgical generator for controlling the generator such that the output of the generator drives the tissue impedance along a predetermined impedance curve.

BRIEF DESCRIPTION OF THE DRAWINGS

Various embodiments will be described herein below with reference to the drawings wherein:

FIG. 8A shows an ideal curve for voltage versus time used for voltage control by the closed loop control system of FIG. 1;

DETAILED DESCRIPTION

Figure 1:
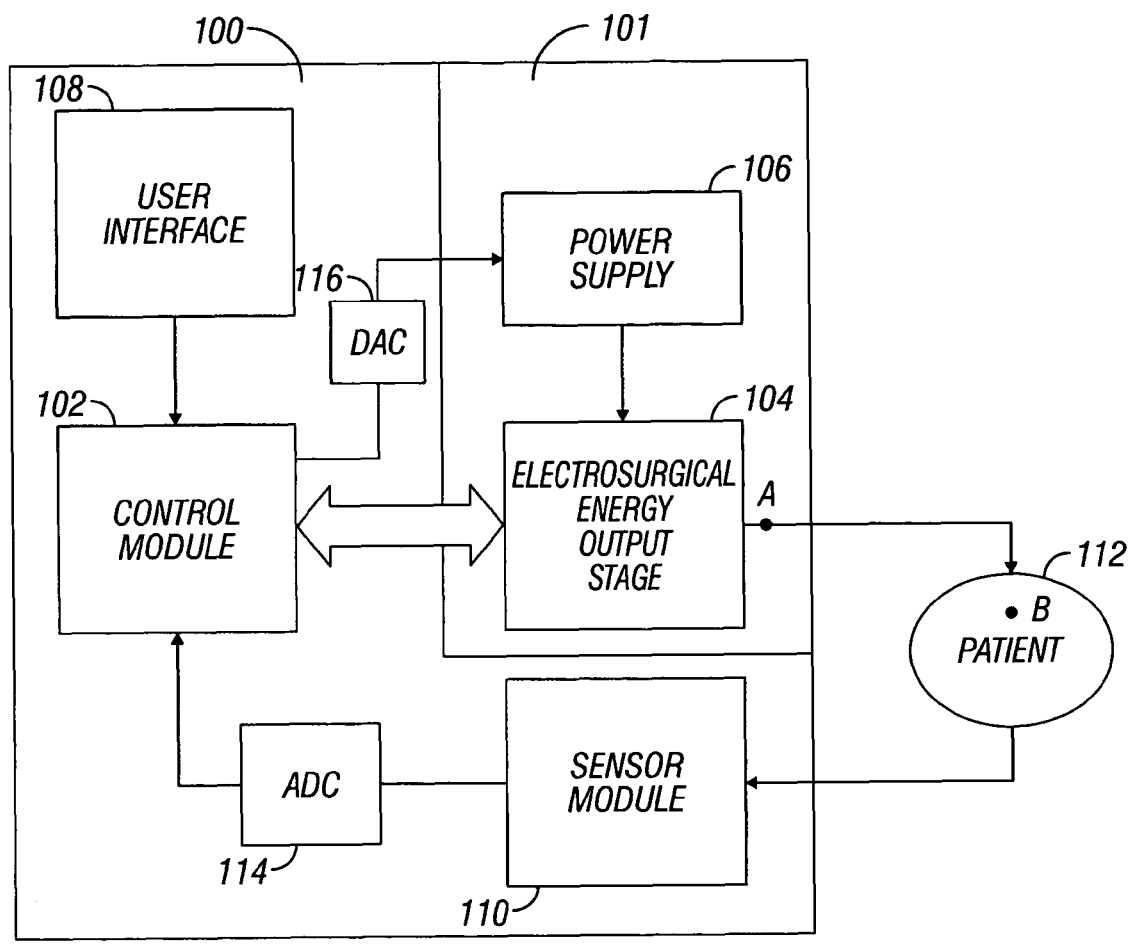
FIG. 1 is a schematic diagram of a closed-loop control system for use with an electrosurgical generator according to the present disclosure.

Reference should be made to the drawings where like reference numerals refer to similar elements throughout the various figures. Referring to FIG. 1, there is shown a schematic diagram of one embodiment of the presently-disclosed closed loop control system 100 for use with an electrosurgical generator 101. Control system 100 includes a control module 102, user interface 108 and sensor module 110. The control module 102 is operatively connected to the generator 101. The control module 102 controls energy delivery by an electrosurgical instrument to a patient. A typical electrosurgical instrument includes an end-effector having jaws for grasping, dissecting and/or clamping tissue, such as for constricting vessels, and further includes at least one delivery device for delivering surgical energy to the patient. Electrosurgical instruments utilize both mechanical clamping action and surgical energy to facilitate hemostasis by energizing the tissue and blood vessels to coagulate, cauterize and/or seal tissue.

In the case where the generator 101 is an electrosurgical generator, the generator 101 preferably includes an electrosurgical energy output stage 104 and a power supply 106. Preferably, the power supply 106 generates RF energy, and the output stage 104 modulates the RF energy and delivers the modulated RF energy as electrosurgical energy to a patient 112 via the delivery device, including at least one electrode (not shown). As can be appreciated, the electrode(s) may be configured as monopolar, bipolar or macro-bipolar. Further, the electrosurgical instrument may be configured as suitable for performing laparoscopic, endoscopic or open surgery.

The sensor module 110 senses various electrical and/or physical parameters or properties at the operating site and communicates with the control module 102 to regulate the electrosurgical output from the output stage 104 and/or the power supply 106. It is envisioned that the sensor module 110 may be configured to measure, e.g., sense, various electrical, physical and/or electromechanical conditions at the operating site, such as: voltage, current, power and impedance across the tissue (tissue impedance), tissue temperature, leakage current, applied voltage, applied current, tissue thickness, volume of tissue between jaws of electrosurgical instrument, tissue light transmission, reflectivity and/or absorption properties, tissue moisture content level, tissue elastomeric properties, tissue viability and/or tissue reactive pressure. Preferably, the sensor module 110 measures one or more of these conditions continuously or in real-time such that the control module 102 can continually modulate the electrosurgical output according to a specific purpose or desired surgical intent. More particularly, analog signals provided by the sensor module 110 which correspond to the sensing are converted to digital signals via an analog-to-digital converter (ADC) 114, which in turn are provided to the control module 102. One such sensor module of a control system for controlling medical generators is described in commonly owned U.S. patent application Ser. No. 10/427,832, entitled "METHOD AND SYSTEM FOR CONTROLLING OUTPUT OF RF MEDICAL GENERATOR", filed on May 1, 2003, which is a continuation-in-part of U.S. application Ser. No. 10/073,761, filed on Feb. 11, 2002, by Wham et al., entitled "VESSEL SEALING SYSTEM", both of which are incorporated herein by reference in their entirety.

Sensors of the sensor module 110 may include at least one sensor for sensing an indication of imminent or actual damage (collateral damage) to surrounding tissue, such as due to thermal spread. The sensor(s) may be located at multiple locations near the surgical site "B", and may sense tissue properties, such as optical characteristics of tissue proximate the surgical site, e.g., opaqueness, light transmission, reflectivity, and/or absorption properties, moisture content, reactive pressure, temperature, viability, elastomeric degree and/or impedance, current, voltage and/or power across the tissue. The control module 102 determines when collateral damage is imminent or occurring and sends control signals to at least one indicator (audio, visual and/or sensory) which may be provided for indicating damage and/or imminent damage to tissue surrounding the surgical site "B". Further, the control module 102 may generate a control signal to the generator 101 to stop the surgical process or to modify the surgical process, such as to reduce the energy output. Thermal spread may further be controlled by utilizing different materials on the electrically conductive surfaces that contact the patient. For example, a heat sink (e.g., a thermally conductive, electrically non-conductive material) may be utilized to absorb heat from the tissue site. Commonly-owned U.S. Application Ser. No. 60/467,027 entitled "ELECTROSURGICAL INSTRUMENT WHICH REDUCES THERMAL DAMAGE TO ADJACENT TISSUE" discloses several different types of materials and jaw configurations which may be utilized to reduce thermal spread to adjacent tissue structures, the entire contents of which being incorporated by reference herein.

The control module 102, thereafter, regulates the generator 101, e.g., the power supply 106 and/or the output stage 104, according to the information obtained from the sensor module 110. The regulation of the generator 101 includes regulation of output energy, including at least the voltage, current, resistance, intensity, power, frequency, amplitude, and/or pulse parameters, e.g., pulse width, duty cycle, crest factor, and/or repetition rate. Further, the control module 102 determines completion of a successful seal, upon which the control module 102 sends a stop signal to the generator 101 for stopping the seal process. The control module 102 then determines when a seal procedure is unsuccessful, terminates the seal procedure appropriately, and sends a signal to a visual or audio indicator (not shown) for indicating that the seal procedure was not successful. It is contemplated that for an unsuccessful seal, where the seal is not completed, the control module 102 may initiate a new seal procedure, including controlling the energy delivery as appropriate.

It is further envisioned that the closed loop control system 100 may be an open loop control system, where at least one selected mapping is consulted during a surgical procedure for adjusting the electrical output over time.

Sampling may employed by the sensor module 110 and/or control module 102. Signals corresponding to sensing by the sensor module 110 may be sampled, such as during the process of converting the signals to digital, and/or by the control module 102 for regulating the generator 101 in accordance with the sampled signals.

The user interface 108 communicates with (e.g., by an electrical or wireless connection) the control module 102 to allow the user to input pre-surgical information and to control various parameters of the electrosurgical energy output to the patient 114. During surgery the user can manually set, regulate and/or control one or more parameters of the delivered electrosurgical energy, such as voltage, current, resistance, intensity, power, frequency, amplitude, and/or pulse parameters, e.g., pulse width, duty cycle, crest factor, and/or repetition rate depending upon a particular purpose or to change surgical intent. Alternatively, the user may input a disease state and the control module 102 may be designed to automatically set the generator 101 with specific energy parameters and particular energy ranges based upon certain disease states or disease conditions. One system for controlling a medical generator in accordance with user entered pre-surgical information is described in commonly owned U.S. patent application Ser. No. 10/427,832, entitled "METHOD AND SYSTEM FOR CONTROLLING OUTPUT OF RF MEDICAL GENERATOR", which is incorporated herein by reference in its entirety. The input information may be used for selecting target data to be used by the control module 102, such as selection of one or more mappings, e.g., ideal curve(s) providing desired inner loop values and/or outer loop values for current, voltage and/or power, as described below.

The control module 102 includes at least one microprocessor capable of executing software instructions for processing data received by the user interface 108 and the sensor module 110, and for outputting control signals to the generator 101, accordingly. The software instructions which are executable by the control module are stored in an internal memory in the control module 102, an internal or external memory bank accessible by the control module 102 and/or an external memory, e.g., an external hard drive, floppy diskette, CD-ROM, etc. Control signals from the control module 102 to the generator 101 may be converted to analog signals by a digital-to-analog converter (DAC) 116. Further, an audio or visual feedback monitor (not shown) may be employed to convey information to the surgeon regarding the seal status, quality and/or completion of an effective tissue seal.

It is contemplated that the control module 102 may include analog and/or logic circuitry, and/or other hardware for processing the sensed values and determining the control signals which are sent to the generator 101, rather than, or in combination with, the microprocessor(s).

In one embodiment, the power supply 106 is a high voltage DC power supply for producing electrosurgical current, e.g., radiofrequency (RF) current. Signals received from the control module 102 control the magnitude of the voltage and/or current output by the DC power supply. The output stage 104 receives the output current from the DC power supply and modulates the energy for generating one or more pulses via a waveform generator (not shown). As can be appreciated, pulse parameters, such as pulse width, duty cycle, crest factor and/or repetition rate are regulated in response to the signals received from the control module 102. Alternatively, the power supply 106 may be an AC power supply, and the output stage 104 may vary the waveform of the signal received from power supply 106 to achieve a desired waveform.

For a bipolar electrosurgical instrument, preferred operating conditions include pressure application in the range of about 3 $kg/cm^2$-16 $kg/cm^2$, a gap distance between electrically conductive surfaces in the range of about 0.001 inches to about 0.015 inches. Preferably, selection of the pressure and gap parameters, in conjunction with control of the generator 101, operate to control application of the surgical energy for achieving the desired surgical results.

As mentioned above, the user interface 108 may be local to or remote from the control module 102. A user may enter pre-surgical data such as the type of electrosurgical instrument being used, the type of electrosurgical procedure to be performed, operating conditions (pressure applied by electrosurgical instrument, gap between electrodes, etc.), desired seal results (e.g., total seal or desired tissue viability seal conditions, such as desired percentage of tissue remaining viable) and/or the tissue type upon which the electrosurgical procedure is being performed. Recognition technology having smart sensors may be employed to relay instrument parameters to the generator 101 and/or control module 102, e.g., a smart system, such as described in commonly owned U.S. patent application Ser. No. 10/718,114 entitled "CONNECTOR SYSTEMS FOR ELECTROSURGICAL GENERATOR", the entire contents being incorporated by reference herein.

It is envisioned that the closed loop control system 100, in particular the sensor module, may include one or more smart sensors which provide feedback to the surgeon relating to one or more of these physical properties. Furthermore, the user may enter commands, such as a target effective voltage, current or power level to be maintained, or a target response, e.g., change in regulation of the power supply 106 and/or output stage 104, in response to changes in sensed values, such as an effective change in voltage, current and/or power level as a function of sensed change values.

It is also envisioned that the user may also enter commands for controlling electrical parameters of the RF energy delivered by the electrosurgical generator, as described above. For example, the user may select one or more ideal curves from a plurality of stored ideal curves accessible by the control system 100, where the selected ideal curve(s) provide target values for sensed properties proximate the surgical site, such as current, voltage, impedance, temperature and/or power. It is envisioned that default values are provided for the above target values and target responses.

The sensor module 110 includes a plurality of sensors (not shown) strategically located for sensing various properties or conditions at or proximate points "A" and/or "B". Sensors positioned at or proximate point "A" (hereinafter referred to as at point "A") sense properties and/or parameters of electrosurgical output from output stage 104, and/or properties, parameters or conditions prior to surgical effect of the currently administered electrosurgical energy during the surgical procedure. For example, sensors positioned at point "A" may be provided with or attached proximate the generator 101.

Sensors positioned substantially at or proximate point "B", which may include tissue surrounding point "B" that is subject to possible collateral damage, (hereinafter referred to as at point "B") sense parameters, properties and/or conditions at or across the operating site prior to the surgical procedure and/or in response to surgical effect during the surgical procedure. Preferably, one or more of these sensors may be included with the electrosurgical instrument, (e.g., on one end effector or opposing end effectors) or positioned and/or attached proximate the operating site. For example, optical sensor(s), proximity sensor(s), pressure sensor(s) and/or temperature sensor(s) may be used to detect certain tissue characteristics, and/or electrical sensors may be employed to sense other parameters of the tissue and/or operating effects. It is noteworthy that point "A" may be located proximate the surgical site "B" at a location where the signals outputted by the generator 101 are propagated before they are applied or approximately when they are applied to the surgical site "B".

The sensors are provided with leads or wireless means for transmitting information to the control module, where the information is provided directly to the control module 102, and/or provided to the control module 102 via the sensor module 110 and/or the ADC 114. The sensor module 110 may include means for receiving information from multiple sensors, and providing the information and the source of the information (e.g., the particular sensor providing the information) to the control module 102.

Figure 2:
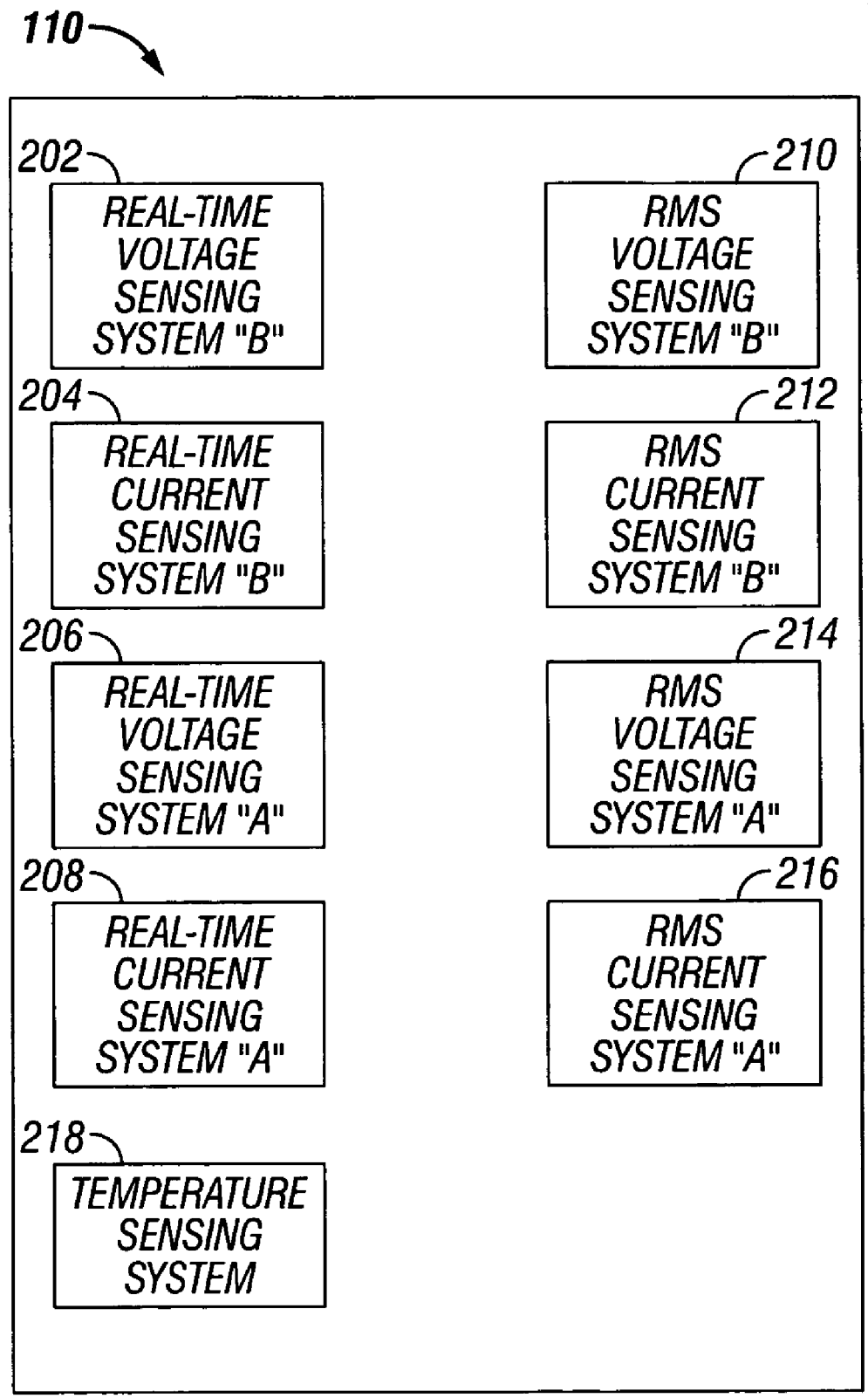
FIG. 2 is a schematic diagram of a sensor module for use with the closed-loop control system of FIG. 1.

With reference to FIG. 2, the inner-working components of the sensor module 110 are shown in greater detail. More particularly, the sensor module 110 preferably includes a real-time voltage sensing system 202 and/or a real-time current sensing system 204 for sensing real-time values for applied voltage and current at the surgical site "B". The sensor module 110 also preferably includes a real-time voltage sensing system 206 and/or a real-time current sensing system 208 for sensing real-time values of signals returned from the patient at a point "A". An RMS voltage sensing system 210 and/or an RMS current sensing system 212 are also included for sensing and deriving RMS values for applied voltage and current at the surgical site "B", and/or an RMS voltage sensing system 214 and/or an RMS current sensing system 216 are included for sensing and deriving RMS values of signals at point "A". A temperature sensing system 218 is preferably included for sensing tissue temperature at the surgical site "B". Real-time and RMS current and voltage sensing systems are known in the art. The sensor module 110 may further include sensors (not shown) for sensing voltage and/or current output by the generator.

The measured or sensed values are further processed, either by circuitry and/or a processor (not shown) in the sensor module 110 and/or by the control module 102, for deriving changes in sensed values and/or calculated values derived from sensed values, such as impedance across the tissue (tissue impedance) at the surgical site "B" and/or comparing real-time sensed values to values of previously sensed values, such as initial values or input reference values. Tissue impedance and changes in tissue impedance may be determined by measuring the voltage and/or current across the tissue and/or calculating changes thereof over time, and comparing the voltage and current values to known and/or desired values that correspond to a selected tissue type of a variety of tissue types for use by the control system 100 to drive electrical output to achieve desired values, such as impedance values and/or change in impedance values.

As can be appreciated, known and/or desired values and ranges for sensed properties that correspond to respective tissue types of one or more tissue types may be calculated and/or stored in at least one mapping, such as an internal look-up table, a "continuous value map" (e.g., an ideal curve) or in an external searchable memory. Preferably, selection of the mapping(s) are based upon user entered and/or sensed pre-surgical parameters, such as operating conditions (pressure applied by electrosurgical instrument, gap between electrodes, etc.), tissue type, tissue thickness, etc. It is contemplated that a representation may be provided to the operator, such as a visual representation on an indicator device (e.g., which may include an indicator light, beep, display device, etc.), during the procedure or following the procedure comparing the actual measured properties to the desired values. Commonly owned U.S. Pat. Nos. 6,398,779, 6,203,541, 5,827,271 and U.S. application Ser. No. 10/073,761 disclose methods for measuring tissue impedance, and are incorporated by reference herein in their entirety.

Figure 8B:
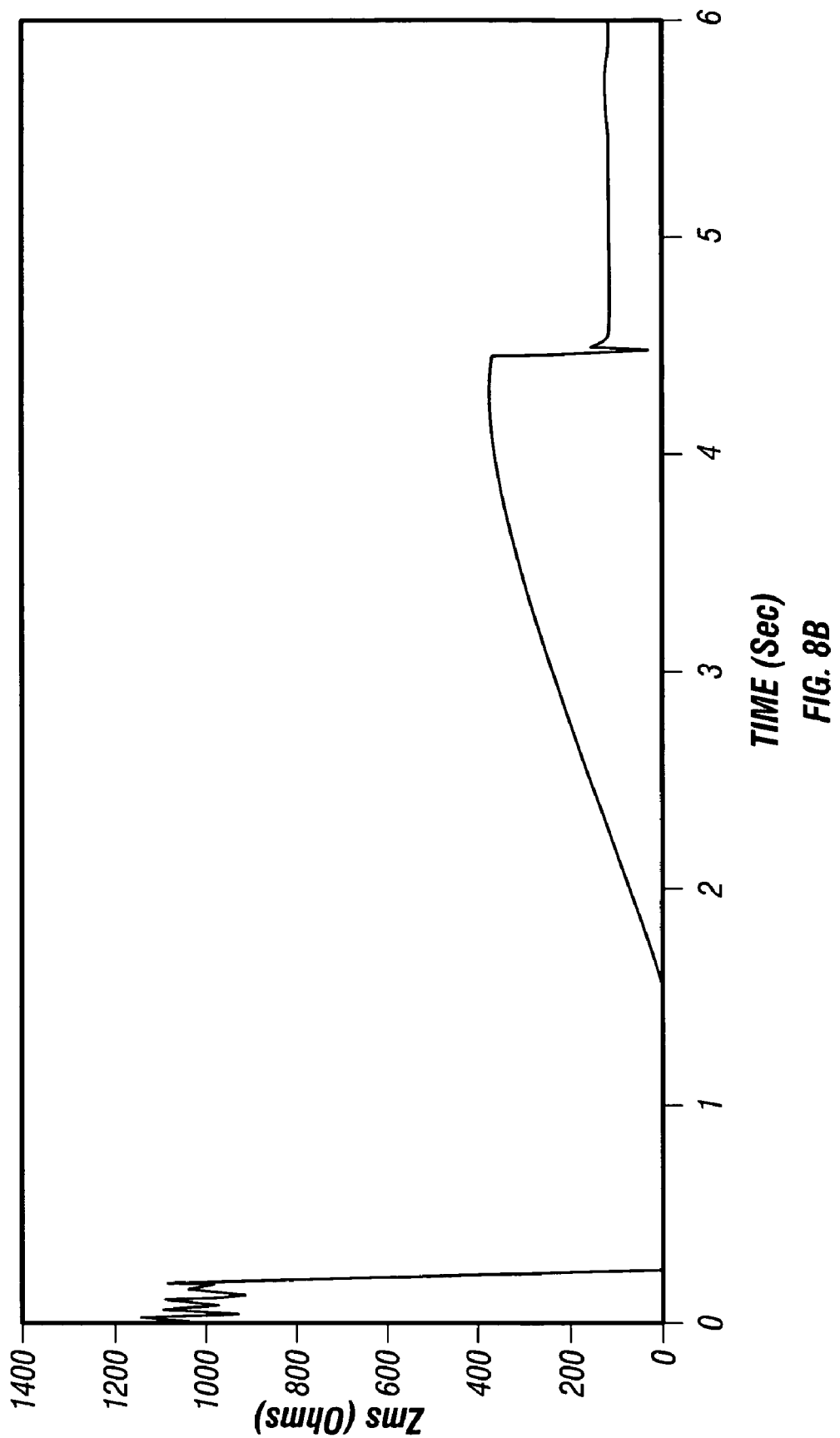
FIG. 8B shows an ideal curve for impedance versus time used for impedance control by the closed loop control system of FIG. 1.
Figure 8C:
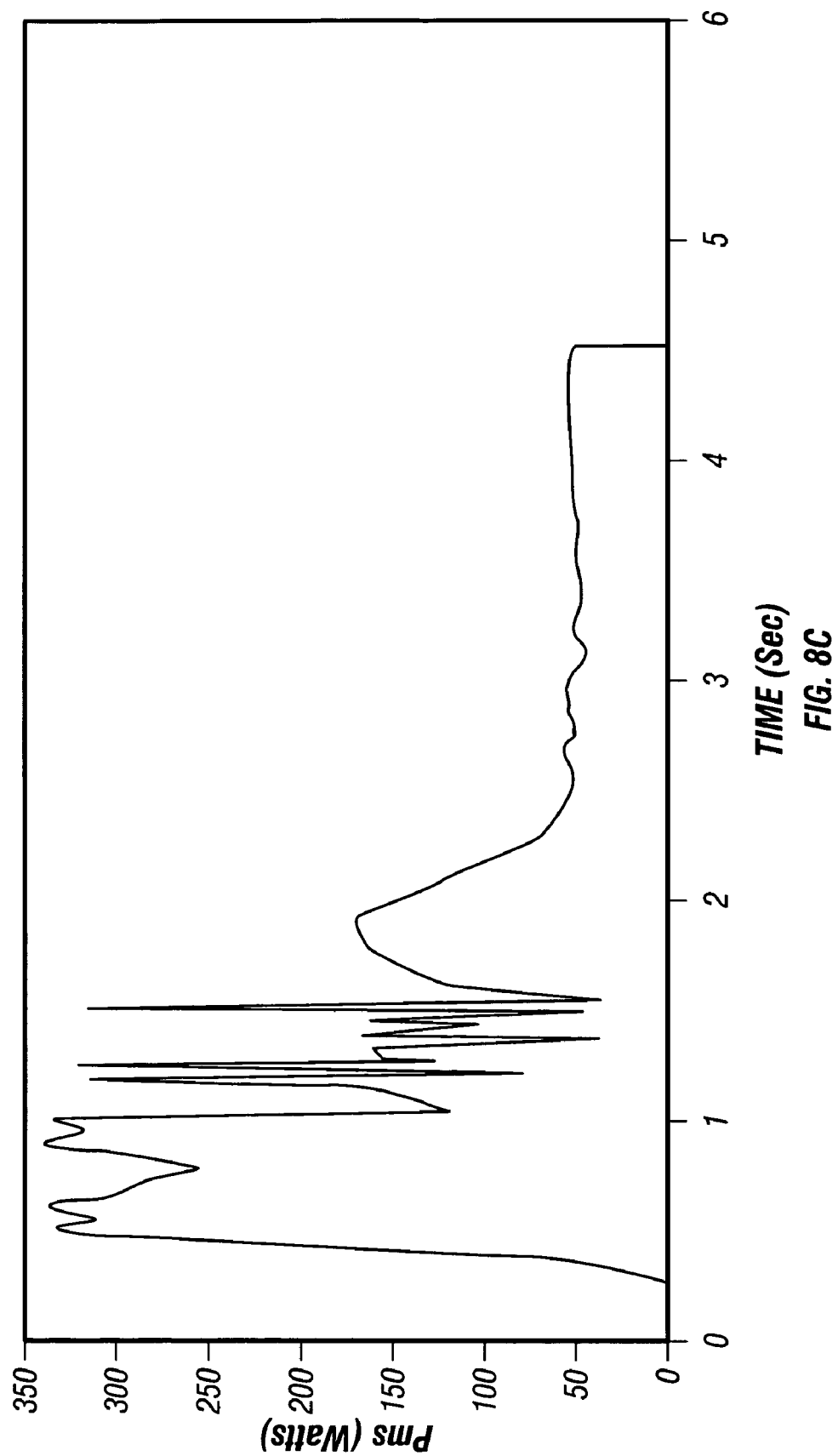
FIG. 8C shows an ideal curve for power versus time used for power control by the closed loop control system of FIG. 1.
Figure 8D:
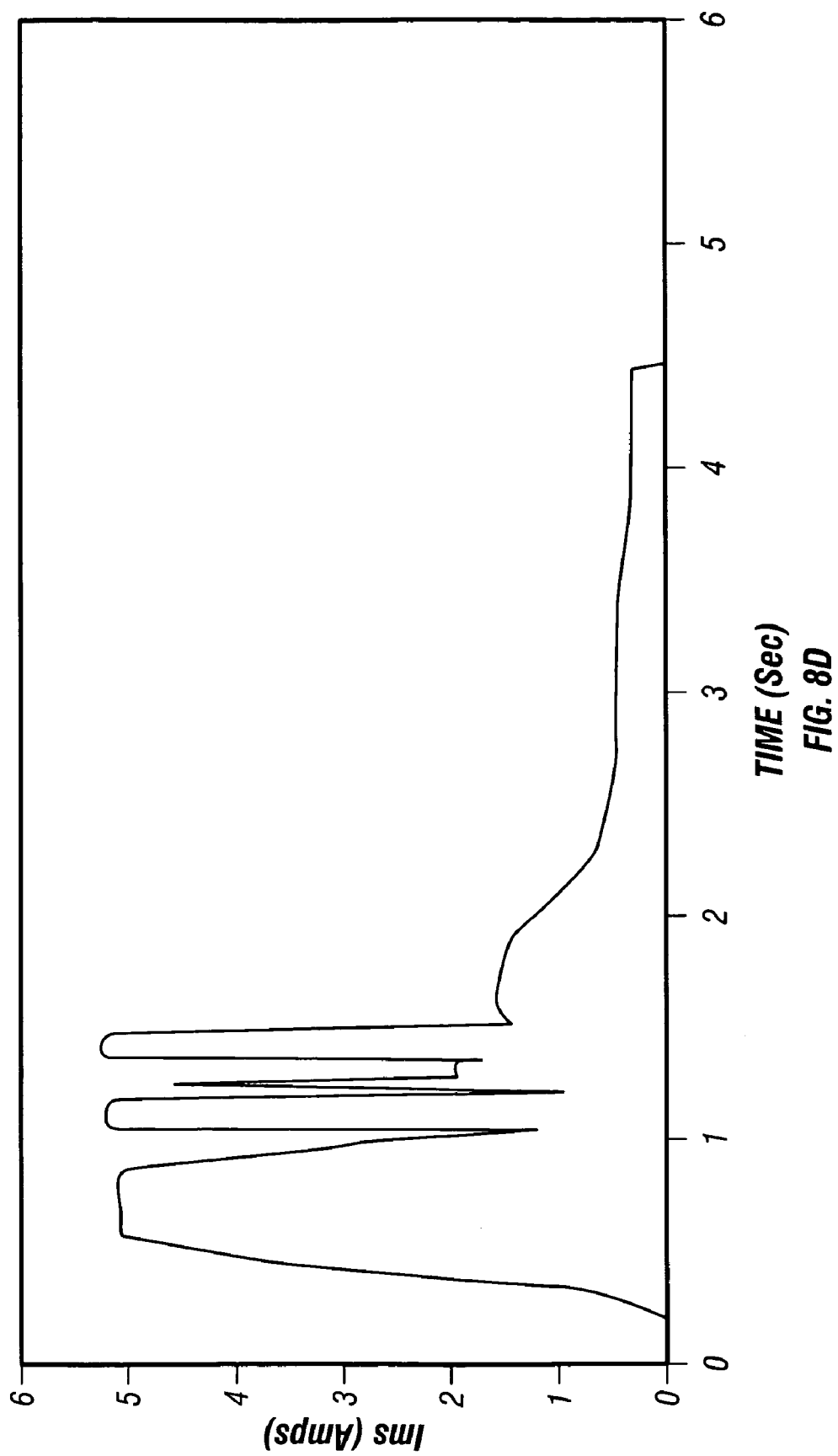
FIG. 8D shows an ideal curve for current versus time used for current control by the closed loop control system of FIG. 1.

Exemplary ideal curves are shown in FIG. 8A-8D, where FIG. 8A shows an ideal curve for voltage versus time. FIG. 8B shows an ideal curve for impedance versus time. FIG. 8C shows an ideal curve for power versus time. FIG. 8D shows an ideal curve for current versus time.

It is envisioned that deriving tissue impedance (or other physical and electrical parameters) from real-time value(s) provides the benefit of monitoring real-time tissue impedance and/or changes in tissue impedance. As the surgical procedure proceeds, it is believed that the tissue impedance fluctuates in response to removal and restoration of liquids from the tissue at the surgical site "B". As the control module 102 monitors the tissue impedance and changes in tissue impedance (or other physical and/or electrical parameters), the control module 102 regulates the power supply 106 and/or output stage 104 accordingly for achieving the desired and optimal surgical effect.

Before beginning an electrosurgical procedure, an operator of the electrosurgical instrument enters pre-surgical information via the user interface 108. Information entered includes, for example, the type of electrosurgical instrument being used, the type of procedure being performed (e.g., desired surgical effect), the type of tissue (e.g., corresponding organ), relevant patient information, and a control mode setting. The control mode setting determines the amount of or type of control that the control module 102 will provide. As mentioned above, one or more sensors (not shown) may also be included to automatically provide information to the control module 102 relating to instrument, tissue type, initial tissue thickness, initial tissue impedance, etc.

Exemplary modes include, but are not limited to, one or a combination of one or more of the following modes: a first mode wherein the control module 102 regulates the selected output energy (e.g., power, current and/or voltage values) at site "A" for maintaining a steady selected value; a second mode wherein the control module 102 regulates the output energy (e.g., power, current and/or voltage value) at site "B" for maintaining a steady selected value; a third mode wherein the control module 102 regulates the output energy by regulating at least one control variable, such as power, impedance, current and/or voltage, at site "A" which is dependent upon (e.g., a function of) time, sensed parameter(s) and/or changes in sensed parameter(s) as measured/sensed during the procedure, e.g., by comparing sensed values to desired values, such as by executing a computer algorithm and/or consulting a mapping; a fourth mode wherein the control module 102 regulates the output energy level by regulating at least one control variable (e.g., power, impedance, current and/or voltage) at site "B", which is dependent upon (e.g., a function of) time, sensed parameter(s) and/or changes in sensed parameter(s) as measured/sensed during the procedure, such as by comparing sensed values to desired values, such as by executing a computer algorithm and/or consulting a mapping. Functions performed on the time value(s) and sensed properties(s) include operations such as calculations and/or look-up operations using a table or map stored by or accessible by the control module 102. The control module 102 processes the selected output level (e.g., power, current and/or voltage values), such as by performing calculations or table look up operations, to determine the content of control signals sent to the generator 101 (e.g., to the power supply 106 and the output stage 104) for controlling the energy output.

The above described regulation of a variable may include recognition of an event, such as a rise, fall, leveling, achieving a target value, achieving a target change over a variable, achieving a target rate of change over the variable and/or achieving a target change of rate of change of a property over a variable for determining what stage of a selected ideal curve has been reached for driving the property along the ideal curve. The variable may be, for example, time or impedance.

The event may be a thermal event, such as a drop or steadying in temperature due to an endothermic phase change of water to vapor and the mass transfer of steam away from the tissue, indicative of entering a dehydration phase of change, which typically occurs at temperatures ranging from 80-130° C. The magnitude of the temperature drop may depend upon the type of tissue, condition of the tissue (e.g., tissue composition and/or water content) and operating conditions (e.g., applied pressure). Another thermal event following dehydration may include a rapid temperature rise due to low heat capacity of dehydrated tissue, indicative of entering a hyalinization phase of change, which typically occurs at temperatures ranging form 110-170° C. Other thermal events may be indicative of a collagen and elastin reformation phase and a completion of seal phase. Thermal events may be reached using most sources of heat or energy, including but not limited to resistive heating, radio frequency, laser and/or ultrasonic energy.

When RF energy is applied, the thermodynamic reaching or completion of a phase change is associated with electrical changes in the tissue. Typically, voltage and impedance values rise rapidly and level out following the completion of a physiological phase change. Current undergoes the inverse reaction, with current levels dropping from a high and steady value to a low and steady value. Consequently, the completion of tissue dehydration and hyalinization can be detected as a negligible rate in change (below a predetermined threshold value, where the threshold value may be selected in accordance with the pre-surgical parameters) of the electrical parameter (e.g., I, V, P, d/dt~0).

It is also envisioned that the control module 102 determines initial settings for control signals to the generator 101 (e.g., to the power supply 106 and/or the output stage 104) by using and/or processing pre-surgical parameters including operator-entered data or settings and/or sensed parameter(s), performing calculations and/or accessing desired values, such as by executing an algorithm and/or consulting a mapping stored by or accessible by the control module 102. The control module 102 selects one or more mappings (e.g., ideal curves) in accordance with the pre-surgical parameters (including operator-entered data or settings and/or sensed parameter(s)) for consultation before beginning the surgery or during the surgery. Once the electrosurgical procedure begins, the sensors of sensor module 110 sense various physical and electrical properties and provide feedback to the control module 102 through the ADC 114 as needed. The control module 102 processes the feedback information in accordance with the pre-selected mode, as well as any additional operator-entered commands entered during the procedure for generating control information. The processing of the feedback information may include: determining the changes of the feedback information over a variable (e.g., time or impedance); rate of change of the feedback information over the variable; and/or relativity of the feedback information to a reference value or corresponding values sensed prior to starting the procedure (pre-surgical values) in accordance with the mode, control variable(s) and ideal curve(s) selected. The control module then sends control information to the power supply 106 and/or the output stage 104. It is contemplated that the generator 101 may be provided with override controls, to allow the operator to override the control signals provided by the control module 102, if needed, e.g., by entering override commands via the user interface 108.

It is also contemplated that the generator 101 and/or control module 102 may be connected remotely, e.g., via a network or the internet, to an off-site database or knowledge base, which includes instrument operating information, mappings, diagnostic information, algorithms or programs which are updated on a regular basis and downloaded to the generator as needed during and/or prior to surgery. As can be appreciated, this enables the user to obtain updated information regarding operation of the instrument, electrical parameters, and ideal curves for optimizing sealing. In addition, this also enables the generator manufacturer to provide updated information on a regular basis. It is also contemplated that the user may be able to receive diagnostic information remotely in this fashion relating to the instruments and/or generators being utilized, either on demand by the user prior to the operation or automatically during a scheduled download.

Figure 3:
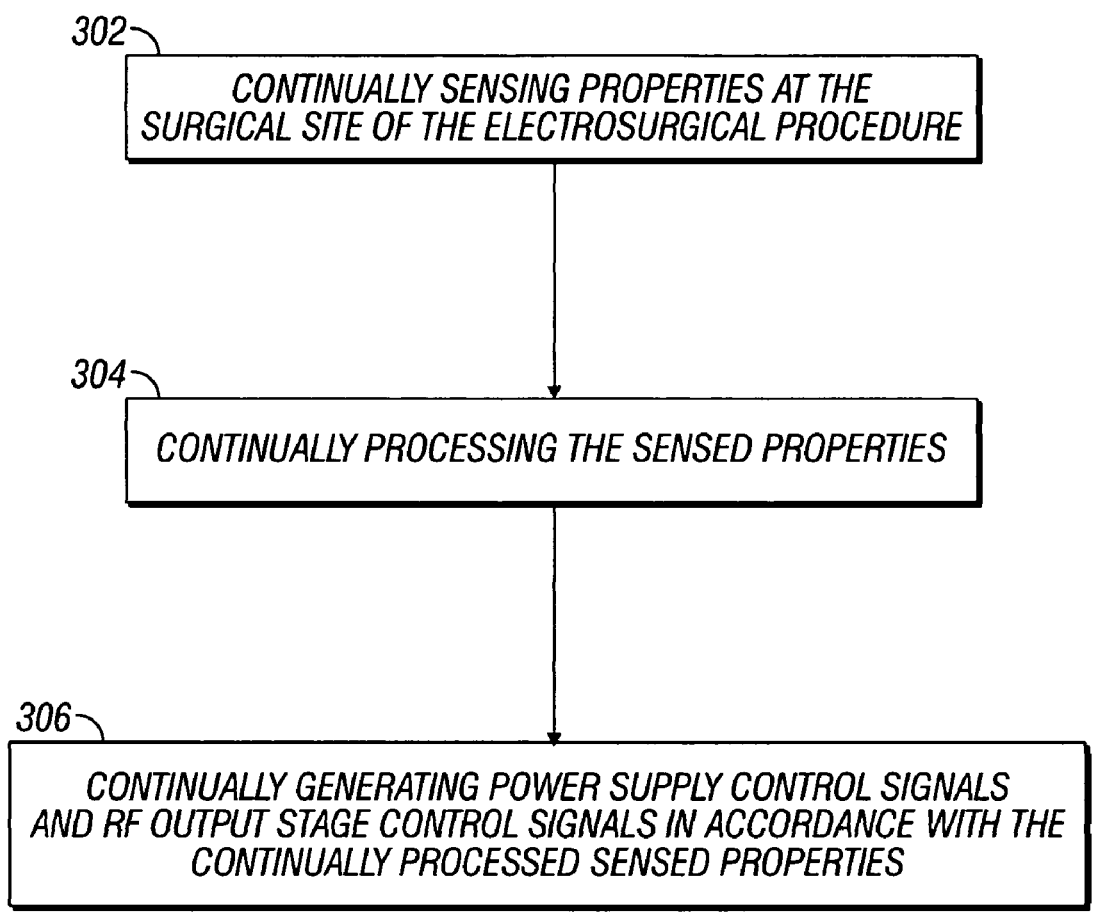
FIG. 3 is a flowchart illustrating one method of operation of the closed-loop control system according to the present disclosure.

FIG. 3 shows a flowchart illustrating a method for controlling operation of the closed loop control system 100 during an electrosurgical procedure in accordance with one embodiment of the present disclosure. At step 302, the method includes continually sensing various physical and/or electrical properties at the surgical site. At step 304, the sensed properties are continually processed. At step 306, the generator 101 continually generates control signals for controlling the energy output until the seal is determined to be complete. Upon determining that the seal is complete, the application of electrosurgical energy is stopped and the post-surgical conditions are determined, such as for determining the seal quality. In this example, the control signals include power supply control signals for controlling the magnitude of the signals output by the generator 101 and/or output stage control signals for modulating the output signals (e.g., controlling pulse parameters) in accordance with the continually-processed sensed properties.

As described above, the sensor module 110 includes a proximity sensor having sensing elements placed at opposite surfaces of the tissue for sensing the distance between the sensing elements for sensing (e.g., measuring) tissue thickness at the surgical site "B", and generating a tissue thickness value. An initial tissue thickness value may be provided to the control module 102 as a pre-surgical parameter. Sensed real-time tissue thickness values and/or changes in tissue thickness values over time (Δ(difference) thickness/Δ(difference) time) may further be provided to the control module 102 during the surgical procedure, where the control module 102 modulates the energy output in accordance with the sensed real-time tissue thickness values, changes in tissue thickness values, rate of change of tissue thickness over time and/or relative value of real-time measured tissue thickness values to the initial tissue thickness value.

As described above, the sensor module 110 further includes a tissue moisture sensor(s) for sensing (measuring) tissue moisture (which is often indicative of tissue type) and generating a moisture content value and/or determining tissue type. It is envisioned that moisture content is determined from tissue compliance, reactive pressure, optical clarity, impedance, reflectivity and/or transmissivity sensed data. The tissue moisture sensor(s) may include an infrared or optical sensor (e.g., a light detector) for sensing (measuring) light or energy generated by a source, such as an infrared or other light source, which is transmitted through, absorbed by or reflected from the tissue, where the sensed value is indicative of tissue moisture content, tissue condition, tissue response to the surgical procedure and/or tissue type of tissue at the surgical site "B".

An initial tissue moisture content value and/or tissue type may be provided to the control module 102 as a pre-surgical parameter. Sensed real-time moisture content values and/or changes in moisture content over time (Δ(difference) moisture content/Δ(difference) time) may further be provided to the control module 102 during the surgical procedure, where the control module 102 modulates the energy output in accordance with the sensed real-time moisture content values, changes in moisture content values, rate of change of moisture content values over time and/or relative value of real-time measured moisture content values to the initial tissue moisture content value. Further, the optics sensor may detect when tissue proximate the surgical site has a glassy appearance, which may be indicative of tissue effects from entry into the hylanization phase. For example, it is envisioned that a glassy appearance may be optically detected by reflectivity, compliance/elasticity or yield strength (e.g., across a jointed electrode). Moreover, the infrared sensors may be designed to provide feedback relating to clarity or density of the tissue before, during or after the sealing process.

In addition, it is contemplated that the sensor module 110 may further include at least one pressure sensor for sensing (e.g., measuring) a reactive force of the tissue against the sensor at the surgical site "B", and generating a pressure value. Tissue typically shrinks during sealing due to dessication of the tissue. Reactive pressure of the tissue on a jaw of the electrosurgical instrument decreases proportionally to the shrinkage. Accordingly, the pressure value and/or changes in the pressure value may provide an indication of the real-time state of the tissue in response to the applied surgical energy, and accordingly, may be useful in determining control of the output energy. It is envisioned that an optical density sensor may be utilized for this purpose.

An initial pressure value may be provided to the control module 102 as a pre-surgical parameter. Sensed real-time pressure values and/or changes in pressure values over time (Δ(difference) pressure/Δ(difference) time) may further be provided to the control module 102 during the electrosurgical procedure, where the control module 102 modulates the electrical signal output in accordance with the sensed real-time pressure values, changes in reactive pressure values, changes in pressure values, changes in gap distance between electrodes, rate of change of pressure values over time and/or relative value of real-time measured pressure values to the initial tissue pressure value. It is envisioned that a look-up table of pre-established or pre-determined values relating to optical density ranges may be cross referenced to determine tissue type, seal completion, etc. it is also envisioned that the control module may be designed to regulate and control the gap distance before and during activation depending upon a particular purpose. For example, one such system is described in commonly-owned U.S. Application Ser. No. 60/470,632 entitled "TISSUE SEALER WITH NON-CONDUCTIVE VARIABLE STOP MEMBERS AND METHOD OF SEALING TISSUE", the entire content being incorporated by reference herein.

It is further envisioned that more than one sensor of the sensor module for sensing a particular property may be provided at different positions, such as along a jaw member of the electrosurgical instrument. For example, proximity sensors positioned at several different positions along the jaw member may sense varying tissue thickness along the jaw member.

Accordingly, the present disclosure provides a closed loop control system 100 for providing continual control of the generator 101 (e.g., power supply 106 and the output stage 104) in response to sensed physical or electrical properties at or proximate the surgical site and/or the output stage. Further, the control system 100 monitors the sensed physical and/or electrical properties at or proximate the surgical site, such as for detecting drops in measured power and/or current to low and stable conditions, and/or detecting achievement of desired tissue viability and/or tissue seal conditions, for determining when the seal process is complete. Upon determination of successful seal completion, a stop signal is generated by the control module 102 for stopping the sealing process.

Otherwise, the control module 102 continues to monitor, receive and process sensed values from the senor module.

If an unsuccessful seal procedure is detected, e.g., when a target property value range (e.g., for temperature, impedance, voltage, current, power, or rate of change thereof, etc.) is not reached in accordance with a predetermined sequence of events or within a predetermined amount of time (e.g., both of which may be user-entered as pre-surgical parameters), a stop signal is generated for stopping the seal procedure. Further indicators of seal quality may include tissue thickness, tissue opaqueness and/or optical tissue properties indicating that the tissue has a rubbery quality to it, indicating that the seal is unsuccessful, or that the tissue has a glassy property, indicating that a successful seal has been achieved. Further, it is envisioned that upon seal completion, if a seal procedure is determined to be incomplete, e.g., the seal formed is insufficient, a new seal procedure may be initiated by the control module 102, where results of the previous seal procedure may be provided as pre-surgical parameters. The sealing process may be stopped upon determining that the seal is complete.

It is further envisioned that the closed loop control system 100 may be an open or closed loop control system, where at least one selected mapping is consulted during a surgical procedure for adjusting the electrical output over time. For an open or closed loop control system, ideal curves may be used that are selected in accordance with the pre-surgical parameters.

Figure 9:
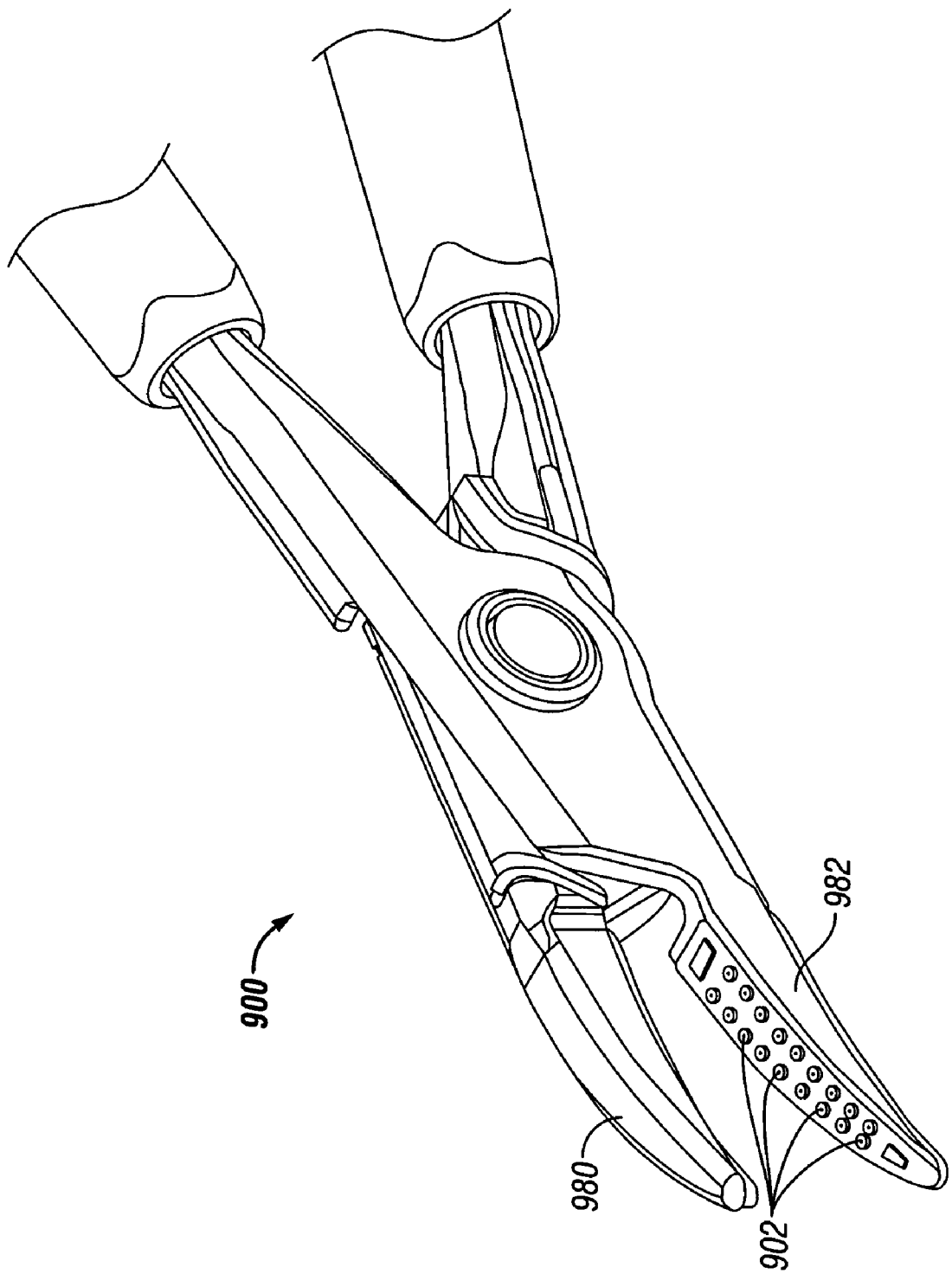
FIG. 9 is a perspective view of an electrosurgical instrument having an electrode assembly according to an embodiment of the present disclosure.

In one embodiment of the disclosure, the control module 102 provides control of energy delivery to a patient by an electrosurgical instrument having at least one array of electrode micro-sealing pads. One such instrument is described in commonly owned PCT Application Ser. No. PCT/US03/08146, entitled "BIPOLAR CONCENTRIC ELECTRODE CONFIGURATION FOR SOFT TISSUE FUSION" the contents of which are incorporated herein in their entirety. With respect to FIGS. 9-11, an electrosurgical instrument 900 is shown having an array of electrode micro-sealing pads 902 disposed across one or both of jaw members 980, 982 for applying RF energy or resistive heating across tissue. In one embodiment of the present disclosure the electrode micro-sealing pads 902 include at least one ring electrode 1022 disposed on one jaw members 982 and at least one post electrode 1012 disposed on the other jaw member 980.

The individual ring electrodes 1022 include an insulating material 1024 disposed therein to form a ring electrode and insulator assembly 1020 and the individual post electrodes 1012 include an insulating material disposed therearound to form a post electrode and insulator assembly 1030. Each post electrode assembly 1030 and the ring electrode assembly 1020 of this embodiment together define one electrode micro-sealing pad 902. Although shown configured in a circular-shape, ring electrode 1022 may assume any other annular or enclosed configuration or alternatively partially enclosed configuration such as a C-shape arrangement. Although the aforementioned configurations for the ring and post electrodes are preferred, it is further envisioned that the electrodes of each array of the micro-sealing pads 902 may have other configurations, provided that the micro-sealing pads 902 are configured for sealing tissue with gaps between sealed portions in which the tissue remains viable.

Figure 10:
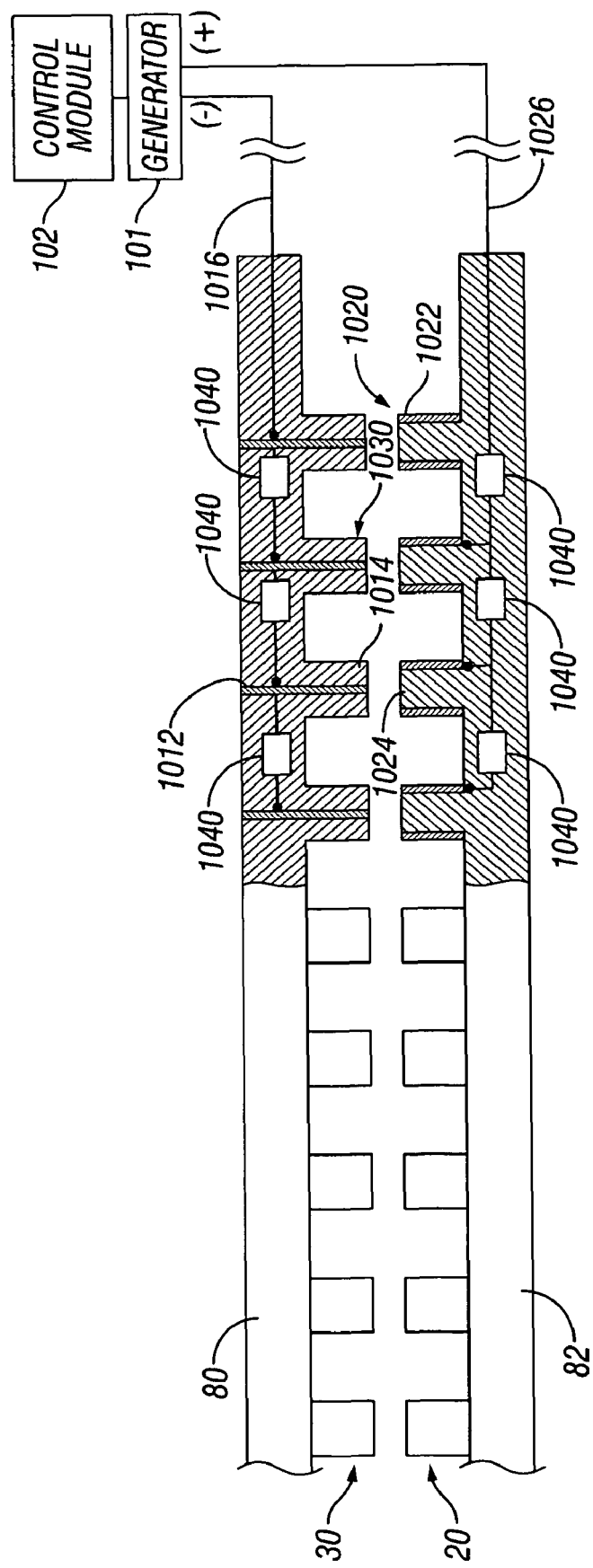
FIG. 10 is a partial, side cross-sectional view of the electrode assembly of FIG. 9, showing a plurality of concentrically-oriented electrode micro-sealing pads disposed on the same jaw member.

As best shown in FIG. 10, the post electrode 1012 is concentrically centered opposite the ring electrode 1022 such that when the jaw members 980 and 982 are closed about the tissue, electrosurgical energy flows from the ring electrode 1022 through tissue and to the post electrode 1012. The insulating materials 1014 and 1024 isolate the electrodes 1012 and 1022 and prevent stray current from tracking to surrounding tissue. Alternatively, the electrosurgical energy may flow from the post electrode 1012 to the ring electrode 1022 depending upon a particular purpose.

Figure 11:
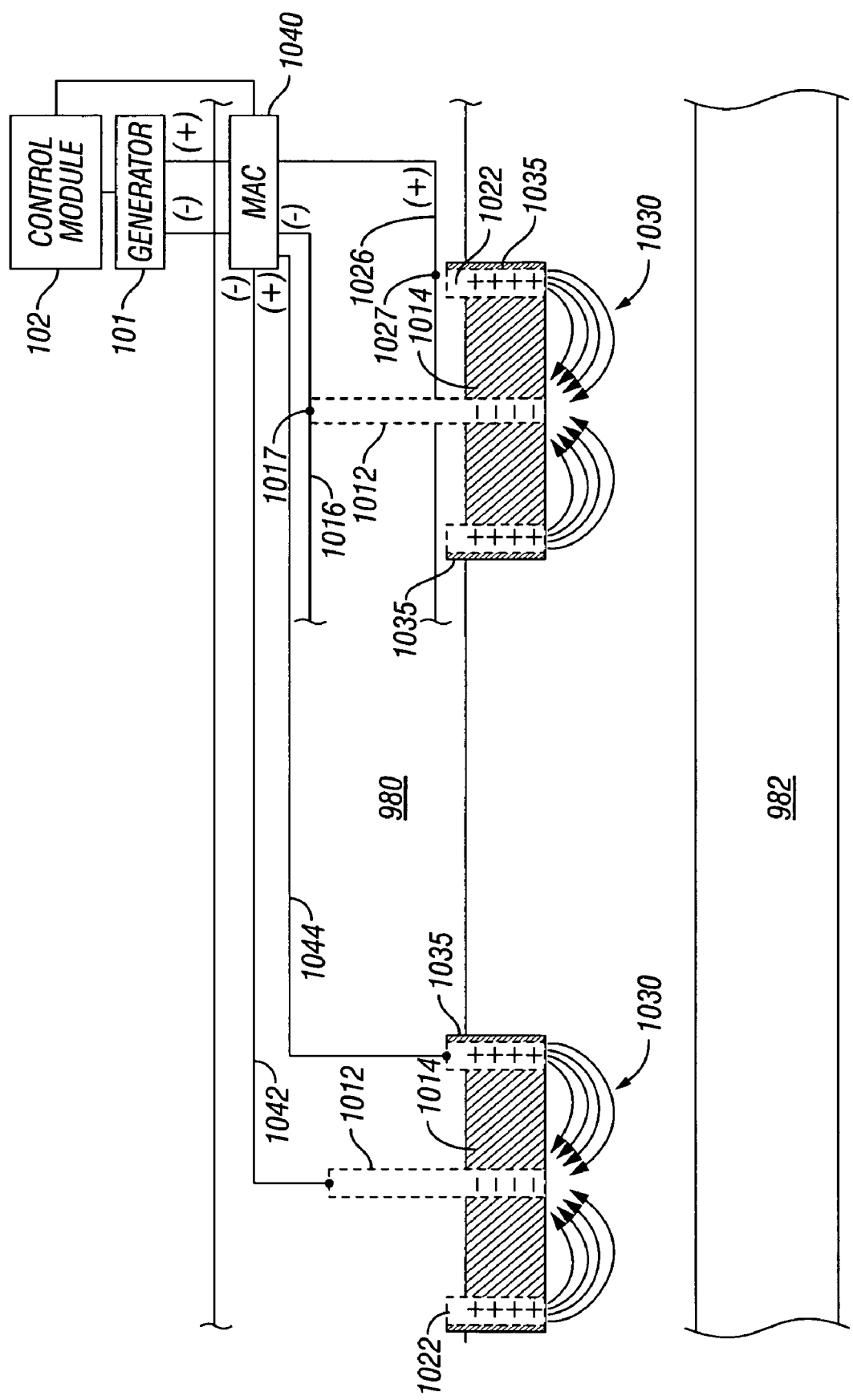
FIG. 11 is schematic view of another embodiment of the electrode assembly showing a plurality of concentrically-oriented electrode micro-sealing pads disposed on the same jaw member and showing the electrical path during activation of the electrode assembly.

FIG. 11 show an alternate embodiment of the jaw assembly, wherein each electrode micro-sealing pad 902 is disposed on a single jaw member, e.g., jaw member 980. More particularly, each electrode micro-sealing pad 902 consists of an inner post electrode 1012 which is surrounded by an insulative material 1014, e.g., ceramic. The insulative material 1014 is, in turn, encapsulated by a ring electrode 1022. Preferably, a second insulative material 1035 (or the same insulative material 1014) encases the ring electrode 1022 to prevent electrical currents from straying to surrounding tissue.

The ring electrode 1022 is connected to the generator 101 by way of a cable 1026 (or other conductive path) which transmits a first electrical potential to each ring electrode 1022 at connection 1027. The post electrode 1012 is connected to the generator 101 by way of a cable 1016 (or other conductive path) which transmits a second electrical potential to each post electrode 1012 at connection 1017. Control module 102 regulates parameters (e.g., intensity, waveform, current, voltage, resistivity, etc.) of the electrosurgical energy supplied thereto in accordance with sensed properties and target values for achieving optimized first and second potentials to enhance the micro-sealing process.

As a result of a flow of electrosurgical energy from the ring electrode 1022, through the tissue and to the post electrode 1012, an intermittent pattern of individual micro-seals is created along and across the tissue. Only the tissue which lies between each micro-sealing pad 902 and/or the opposing jaw member 982 is sealed. The adjacent tissue remains viable which, as can be appreciated, allows blood and nutrients to flow through the sealing site and between the individual micro-seals to promote tissue healing and reduce the chances of tissue necrosis. By selectively regulating the closure pressure and gap distance between the jaws, and electrosurgical intensity, effective and consistent micro-seals 630 may be created for many different tissue types.

It is further envisioned that micro-seal adjustment circuitry (MAC) 1040 is provided for receiving viability control signals from the control module 102 for providing control of individual ring and/or post electrodes for selectively enabling and/or applying a selected potential to the individual ring and/or post electrodes. The micro-seal adjustment circuitry 1040 may be centralized as shown in FIG. 11, or distributed through the array as shown in FIG. 10, or a combination thereof. The micro-seal adjustment circuitry 1040 may include logic circuitry and/or analog circuitry. In one example, the micro-seal adjustment circuitry 1040 may provide selective resistivity to the conductive paths from the generator 101, so that the total resistivity may be different for respective conductive paths to individual ring and/or post electrodes for providing different selected potentials to the individual ring and/or post electrodes.

In another example, in accordance with the viability control signals, at or proximate a first end of one of the jaw members, one or a series of electrodes are electrically connected to a first potential and the corresponding electrodes (either on the same jaw or perhaps the opposing jaw) are connected to a second potential. Towards the opposite end of the jaw member, one or a series of electrodes are connected to a third potential and the corresponding electrodes connected to yet a fourth potential. As can be appreciated, this would allow different types of tissue sealing to take place at different portions of the jaw members upon activation.

The viability control signals may be generated in accordance with pre-surgical parameters (e.g., desired tissue viability) and/or sensed properties, preferably including tissue viability, measured by the sensor module 110 in real-time during the procedure. Further, if a seal formed by a seal procedure was determined to be insufficient (e.g., the ratio of viable tissue to nonviable tissue is too high), a new seal procedure may be initiated by the control module 102, where a different set of selected ring and post electrodes are enabled and/or different corresponding potentials are selected relative to those used for the previous seal procedure.

To seal larger tissue, the operator would grasp the tissue more towards the proximal portion (closer to a handle held by the operator) of the opposing jaw members, and to seal smaller tissue the user would grasp the tissue more towards the distal portion of the jaw members. It is also envisioned that the pattern and/or density of the micro-sealing pads 902 may be configured to seal different types of tissue or thicknesses of tissue along the same jaw members depending upon where the tissue is grasped between opposing jaw members, such as in accordance with sensed information. It is also envisioned that the micro-sealing pads 902 may be arranged in many different configurations across or along the jaw members 280 and/or 282 depending upon a particular purpose. Moreover, it is also contemplated that a knife or cutting element (not shown) may be employed to sever the tissue between a series of micro-sealing pads 902 depending upon a particular purpose. The cutting element may include a cutting edge to simply mechanically cut tissue and/or may be configured to electrosurgically cut tissue.

Figure 4:
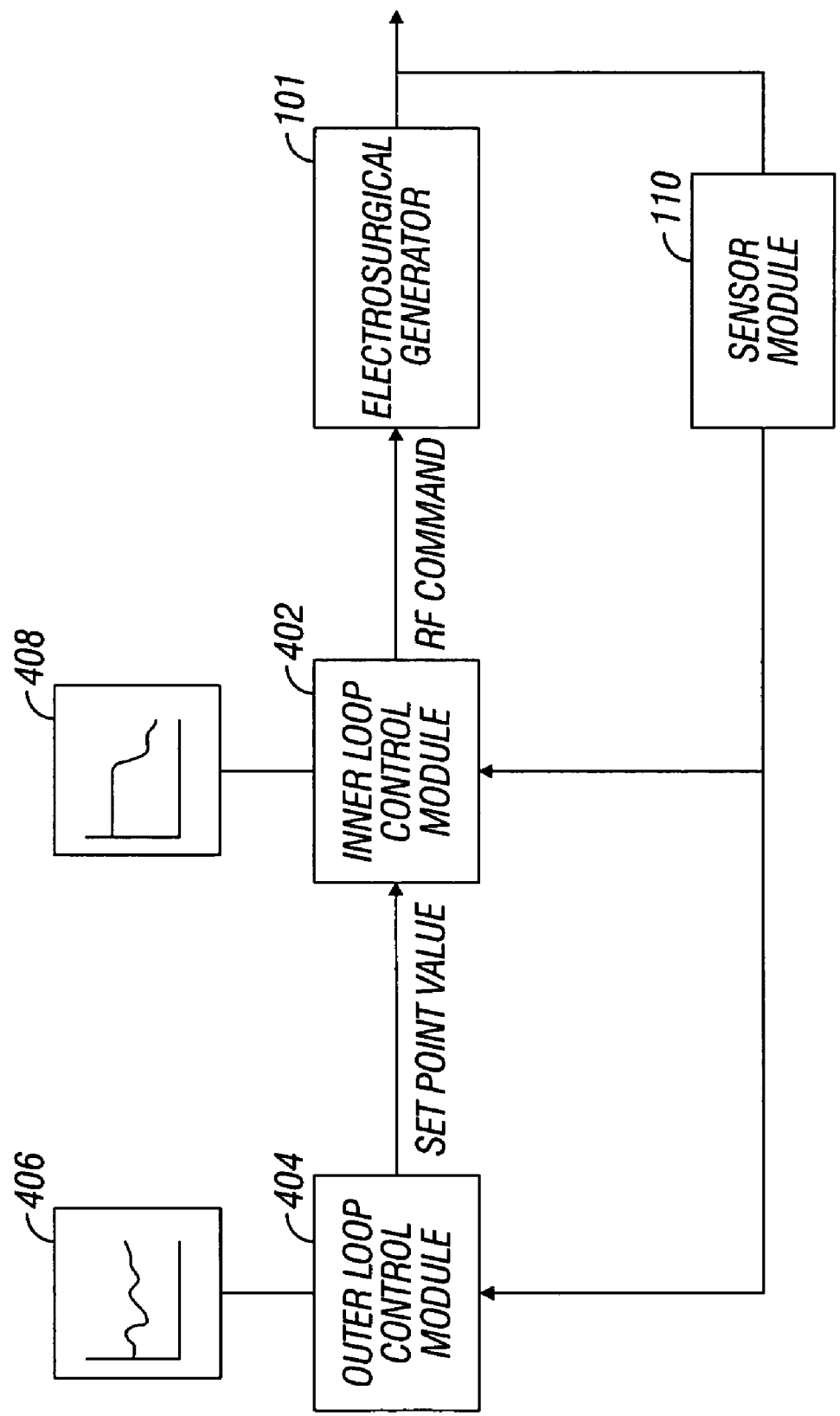
FIG. 4 is a block diagram of a dual loop control system in accordance with another embodiment of the invention.

In an additional embodiment according to the present disclosure and in particular reference to FIG. 4, the control module 102 is provided with two control loops, an inner loop controlled by inner loop control module 402 and an outer loop controlled by outer loop control module 404. Preferably, the inner and outer loop control modules 402, 404 are software modules executable by a processor of the control module 102. The inner and outer loop control modules 402, 404 both receive signals generated by sensor module 110.

The inner loop control module 402 controls the amount of current, voltage and/or power delivered to the tissue for controlling a variable, e.g., current (I), voltage (V) and/or power (P), sensed at the tissue and/or calculated from sensed values, until a desired event occurs, e.g., the achievement of a target dz/dt or impedance rise. The target dz/dt is typically achieved when a target impedance value is reached, e.g., a target impedance value of 200-500 ohms for lung and bowel tissue, which may differ for other types of tissue. Occurrence of the desired event indicates that a stage in the seal cycle has been reached at which current, voltage and/or power delivery to the tissue should be changed (in this example, decreased) for achieving the desired tissue effects. The control variable is controlled to change during the course of the seal cycle according to the impedance value (or other sensed and/or derived values), as determined by generator limitations (e.g., power, current, voltage) and surgical limitations (e.g., maximum limits for application of energy to tissue).

With continued reference to FIG. 4, the inner loop control module 402 continually receives real-time sensed values, such as current (I) and/or voltage (V), power (P) and impedance (Z) from the sensor module 110, and may perform calculations on the received values for deriving additional real-time values (for example, P and Z and/or rate of change may be derived). Desired inner loop values for I, V, and/or P are obtained by accessing at least one stored inner mapping of continuous values 408, look-up table or equivalent, where preferably the inner mapping 408 is in accordance with a function of impedance. Preferably, the inner loop control module 402 consults the inner mapping 408 for obtaining the desired inner loop value which corresponds to the impedance currently being sensed and derived. Preferably, the inner mapping(s) 408 is selectable from a plurality of stored mappings accessible by the control system 100 in accordance with the pre-surgical parameters, such as tissue type.

An algorithm is used to compare the real-time value of I, V and/or P to the respective desired inner loop value and output an RF command to the generator 101 accordingly for achieving the desired inner loop value without exceeding the desired inner loop value, e.g., the RF command raises the target current, voltage and/or power output by the generator 101 when the real-time value for I, V and/or P is lower than the respective desired inner loop value for I, V and/or P, and vice versa. It is contemplated that the RF command controls waveform parameters of electrosurgical energy output by the generator 101, including current, power, voltage, duty cycle, frequency and/or waveshape, etc. It is further contemplated that the inner loop is used without the outer loop for achieving the desired tissue effect.

The outer loop control module 404, layered over the inner loop control module 402, provides additional control of a variable for reaching a desired output value or effect. For example, control of the variable may monitor/regulate the rate of change of impedance of the tissue (e.g., sensed and calculated). In different embodiments, the variables controlled may include temperature, rate of change of temperature, and/or the energy input to the tissue. Outer loop control module 404 continually receives sensed values, such as I, V and/or temperature (T) from the sensor module 110 at a time "t" and performs calculations on the sensed value(s) and preferably stored values for deriving values such as rate of change of impedance and/or rate of change in temperature. For example, the value for change in impedance (dz/dt) may be obtained in accordance with equation (1) below. Change in temperature T (dT/dt) may be calculated similarly.

$$dz/dt = (Z - Z\_OLD)/(t - t\_OLD);$$

$$Z\_OLD = Z; \quad (1)$$

where Z is the impedance in accordance with values measured at time (t); and
Z_OLD is the stored impedance in accordance with values measured at a previous time interval at time (t_OLD)

With continued reference to FIG. 4, outer loop desired values for the control variable are obtained by accessing a stored outer mapping of continuous values 406, or alternatively a table or equivalent and comparing the real-time derived value obtained at time (t) to the value accessed at time (t). The desired rate of change according to outer mapping 406 may be steady, or may depend on the stage of the seal cycle and change over time. Preferably the outer mapping 406 is selectable from a plurality of stored mappings accessible by the control system 100 in accordance with the pre-surgical parameters, such as tissue type. The tissue is in a dynamic state during the seal procedure, and the outer loop monitors the rate of change throughout the procedure to determine the degree to which the desired rate of change is being achieved. When the control variable is temperature, a temperature map may be used for outer mapping 406 in which desired temperature is plotted versus time. When the control variable is rate of change in temperature, a rate of change in temperature map may be used for outer mapping 406 in which desired temperature is plotted versus time. Power may be controlled in a similar fashion by accessing a stored power mapping selectable from a plurality of stored mappings which were derived for specific tissue types.

During a procedure, a variety of methods may be used for controlling dz/dt (the slope of the line plotted for real-time Z (Zrt) vs. time) by monitoring dz/dt and controlling the energy delivery. In an exemplary method, described as a trajectory method, a target line for desired Z vs. time (t) is provided, via a mapping, e.g., a continuous value mapping, a look up table or a formula, where the target line has a slope that is a target slope, e.g., target dz/dt. Zrt is obtained (measured and calculated) at time (t), and the desired value for Z (Zd) is determined by accessing the value for Zd on the desired line at time (t). Zrt is compared to Zd and the set point is adjusted for regulating the energy output (I, V and/or P) via the inner loop control module 402 in accordance with the magnitude of the differential. Similarly, dT/dt may be controlled by providing and consulting a target line for desired T plotted vs. time having a target slope, target dT/dt.

An algorithm is used to compare the real-time sensed/calculated value of rate of change of impedance, temperature, rate of change of temperature and/or energy obtained at time (t) to the respective desired outer value corresponding to time (t) obtained from the outer mapping 406 or the target line for determining if the desired outer value is met. If the desired outer value is not being met, the outer loop module 406 determines the differential, such as the ratio of the difference between the real-time value and the desired outer value to the desired outer value, and generates a set point value indicative of the determined differential, and provides the set point value to the inner loop module 402. The set point value is raised when the real-time value for rate of change of impedance, temperature and/or rate of change of temperature is lower than the respective desired outer value for rate of change of impedance, temperature and/or rate of change of temperature, and vice versa. Accordingly, the magnitude of the set point value is proportional to the difference between the real time and the desired values.

The set point value is preferably a ratio signal for altering the inner mapping 408 by raising or lowering a plotted curve of the inner mapping 408 along the y-axis. Preferably, the ratio signal is a proportional integral derivative (PID) control signal, as is known in the art. The inner loop control module 402 responds instantaneously by accessing the altered inner mapping 408 for obtaining a desired inner value from the outer loop, comparing the real-time value of the control variable, generating an RF command for achieving the desired inner value without exceeding the desired inner value, and outputting the RF command accordingly to the generator 101 for controlling voltage, current and/or power needed for achieving a desired tissue effect.

With continued reference to FIG. 4, preferably, the outer loop control module 404 uses the real-time value of rate of change of impedance, temperature, rate of change of temperature, and/or total energy delivered to determine if a desired outer value has been reached which indicates completion of a seal. More specifically, monitoring attainment of a target temperature has successfully been used for determining seal completion. Further, drops in measured power and/or current to low and stable conditions are typically indicative of the completion of work relative to the change of phase needed for tissue sealing. Upon determination of seal completion, a stop signal is generated for stopping the sealing process. Otherwise, the outer loop continues to monitor, receive and process sensed values from the senor module 110.

In one exemplary scenario, current control is used until a breakpoint where an impedance having a value of Zlow is reached, after which voltage control is used. During current control, preferably the change in current is regulated for maintaining a constant positive value. During voltage control, preferably, the voltage is regulated for maintaining a constant desired value. In another exemplary scenario, current control is used until a breakpoint where an impedance having a value of Zhigh is reached, after which voltage control is used. During current control, preferably the current is regulated for maintaining a constant desired value. During voltage control, preferably the change in voltage is regulated for maintaining a constant negative value.

It is contemplated that the generator 101 may include a module for generating resistive heat, in addition to or instead of the power supply 106 and/or the output stage 104 for generating electrosurgical RF energy, where the control module 102 regulates the resistive heat applied to the tissue for achieving the desired tissue effect. The control module 102 responds to sensed tissue temperature or other sensed properties indicative of tissue temperature, accesses at least one mapping, data table or equivalent using the sensed values for obtaining desired output current or resistivity values, and outputs a command signal for controlling output heat resistivity. Preferably, the module for producing resistive heat includes a current source and/or a variable resistor which are responsive to the command signal for outputting the desired current or providing a desired resistance, respectively.

It is further contemplated that the generator 101 may also include a module for generating laser energy or ultrasound energy, in addition to or instead of the power supply 106 and/or the output stage 104 for generating electrosurgical RF energy, where the control module 102 regulates the laser energy or ultrasound energy applied to the tissue for achieving the desired tissue effect. The control module 102 responds to sensed physical and/or electrical properties of the tissue, such as temperature or other properties indicative of tissue temperature, accesses at least one mapping, data table or equivalent, uses the sensed values for obtaining desired output values from the at least one mapping, and outputs a command signal for controlling parameters (intensity, pulse rate, etc.) of the output laser energy or ultrasound energy.

It is envisioned that in another embodiment of the disclosure, the sensor module 110 senses at least one property associated with the surgical site during at least one of a pre-surgical time prior to a surgical procedure, a concurrent-surgical time during the surgical procedure, and a post-surgical time following the surgical procedure for generating at least one signal relating thereto. The control module 102 receives and processes at least a portion of the at least one signal using at least one of a computer algorithm and a mapping, and generates control signals in accordance with the processing, and provides the control signals to the generator 101 for controlling the generator 101. Preferably, processing of the signals relating to pre-surgical conditions includes determining type of tissue at the surgical site.

Preferably, the sensor module 110 senses at least one property as a pre-surgical condition sensed at a pre-surgical time prior to a surgical procedure, as a concurrent surgical condition sensed during the surgical procedure and/or as a post-surgical condition sensed following the surgical procedure or at the end of the surgical procedure. Preferably, the sensor module 110 senses two surgical conditions (or changes in surgical conditions over time) selected from at least two of pre-surgical conditions, concurrent surgical conditions and post-surgical conditions for generating at least one signal relating thereto.

Pre-surgical conditions (sensed and/or user entered) include but are not limited to: the type of electrosurgical instrument being used, operating conditions (pressure applied by electrosurgical instrument, gap between electrodes, etc.), desired seal results (e.g., total seal or desired tissue viability seal conditions, such as desired percentage of tissue remaining viable at seal site), ideal curve(s) selected from a plurality of stored ideal curves accessible by the control system 100 providing target values for surgical parameters and/or tissue properties, tissue temperature, tissue thickness, volume of tissue between jaws of electrosurgical instrument, tissue light transmission, reflectivity and absorption properties, tissue moisture content level, tissue elastomeric properties, tissue viability (e.g., a percentage of viable tissue within a specified area of tissue) and/or tissue reactive pressure of tissue at the surgical site "B". Furthermore, a pre-surgical sensing of tissue electrical properties, such as impedance, power, leakage current, applied voltage and/or current across the tissue, may be obtained by applying a pre-surgical energy (where the energy is not applied at a surgical level) and sensing the properties across the tissue.

Concurrent conditions include but are not limited to: voltage, current, power and impedance across the tissue, leakage current, applied voltage, applied current, total energy applied, total power applied, tissue temperature, tissue thickness, volume of tissue between jaws of electrosurgical instrument, tissue light transmission, reflectivity and absorption properties, tissue moisture content level, tissue elastomeric properties, tissue viability, tissue compliance and/or tissue reactive pressure of tissue at the surgical site "B", changes thereof, rate of change thereof and/or relativity thereof to pre-surgical corresponding sensed values.

The post-surgical conditions include but are not limited to tissue impedance, leakage current, voltage and/or current which were applied during the procedure, tissue temperature, tissue thickness, volume of tissue between jaws of electrosurgical instrument, tissue light transmission, reflectivity and absorption properties, tissue moisture content level, tissue elastomeric properties, tissue viability and/or tissue reactive pressure of tissue at the surgical site "B". The post-surgical conditions may be measured following the surgical procedure, or may be final measurements taken upon determining that the seal procedure is completed. Preferably, at least one property sensed during the post-surgical condition is indicative of the quality of a tissue seal formed during the surgical procedure.

In another embodiment according to the present disclosure, the impedance across the tissue proximate the surgical site "B" is continually measured during the tissue sealing or tissue fusion process and this information is relayed back to the control module 102 where the information relating to the impedance is monitored and processed. The control module 102 generates control signals for regulating the generator 101 for producing regulated energy that is delivered to the patient for driving the impedance across the tissue at the surgical site B along an ideal impedance curve, such as the curve 500 identified in FIG. 5. In accordance with the ideal impedance curve, rapid sealing or fusion (approximately 2-15 sec.) can be achieved for soft tissue structures, including but not limited to isolated vessels, ducts, lymph nodes, vascularized tissue bundles, lung, liver, intestinal tissue, spleen and stomach.

As can be appreciated by the present disclosure, tissue fusion is optimized by preventing both over-heating of tissue and under-heating of tissue. For example, overheated tissue seals which are characterized by an uncontrolled impedance rise are known to rupture because the tissue vaporizes excessively (e.g., dries out) prior to reformation of the tissue structure, leading to a weak seal. Overheated tissue may also lead to unwanted collateral damage to surrounding tissue or an overactive immune response. In contrast, under-heated tissue seals, which are characterized by an insufficient impedance rise, are also known to create weak seals prone to leakage because the tissue never truly reforms into a fused mass, e.g., there is an incomplete tissue response.

Figure 5:
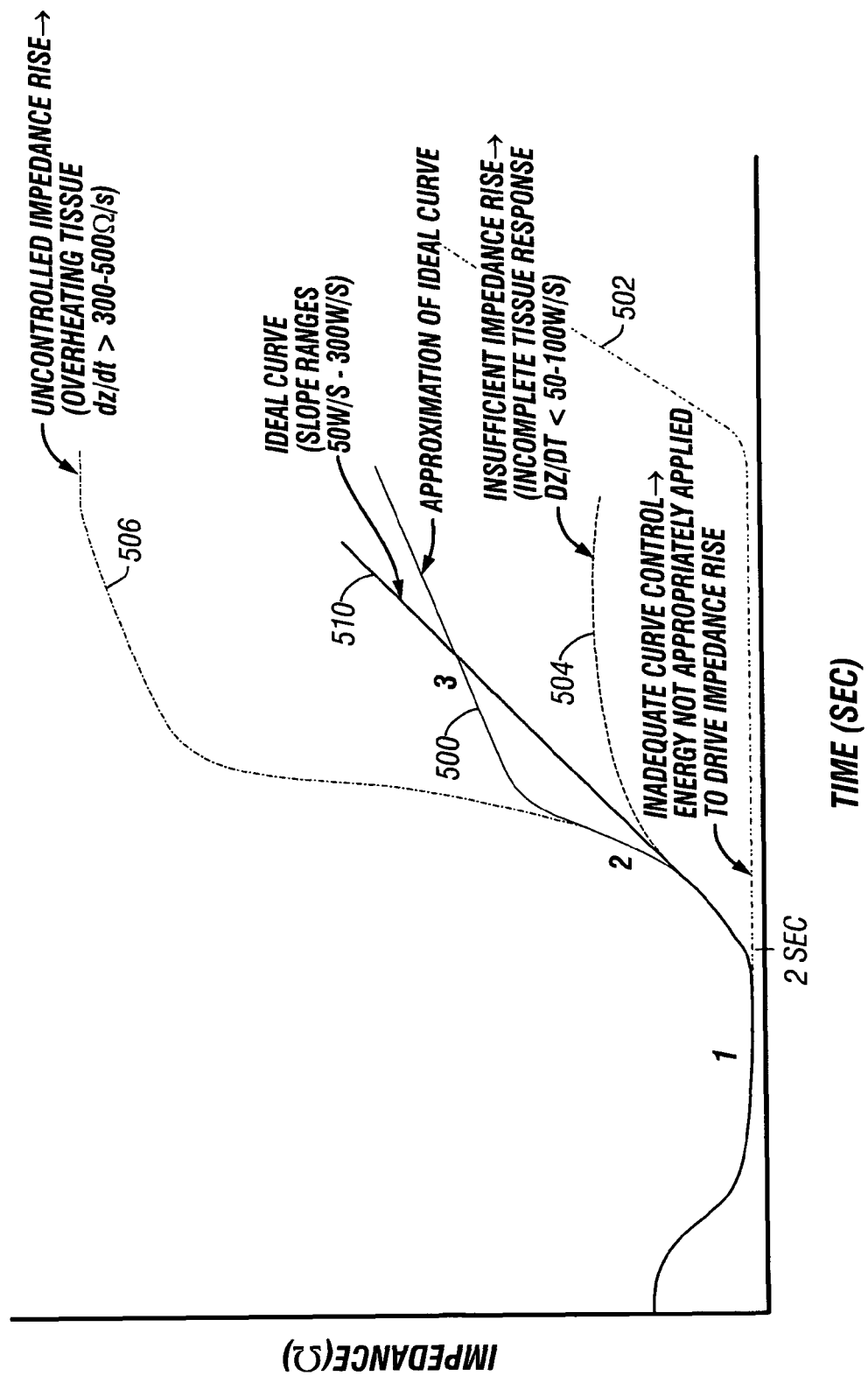
FIG. 5 is a schematic representation of a variety of impedance curves over time with annotation.

As best shown in FIG. 5, to drive the impedance across the tissue along the ideal impedance curve 500 to optimize tissue fusion, certain sealing stages must be carefully controlled in order to effect a proper transition between stages, where the stages may be characterized by different slopes. For example, during stage "1", it is important to control the energy to the tissue to drive the tissue response to insure a timely and rapid transition into an impedance rise across the tissue. During the second stage, e.g., stage "2", the impedance rise should be controlled such that sufficient energy is delivered to vaporize tissue moisture without overheating tissue or causing thermal damage to surrounding tissue. During stage "3", the energy delivered to the tissue should be controlled to permit reformation of structural elements of the tissue, e.g., collagen and elastin, while the rise in temperature over time is generally kept constant, which is ideal for tissue reformation. As mentioned above, uncontrolled impedance rise leads to overheating of tissue, and insufficient impedance rise leads to an incomplete tissue response.

Curve 502 shows an impedance curve in which the energy output by the generator 101 was not appropriately controlled for timing the impedance rise within an acceptable window. Curve 504 shows an impedance curve in which the energy output by the generator 101 was not appropriately controlled for driving the impedance rise, and accordingly, the tissue response is insufficient. Curve 506 shows an impedance curve in which the energy output by the generator 101 was not appropriately controlled, leading to uncontrolled impedance of the tissue proximate the surgical site B, resulting in overheating of the tissue.

Figure 7:
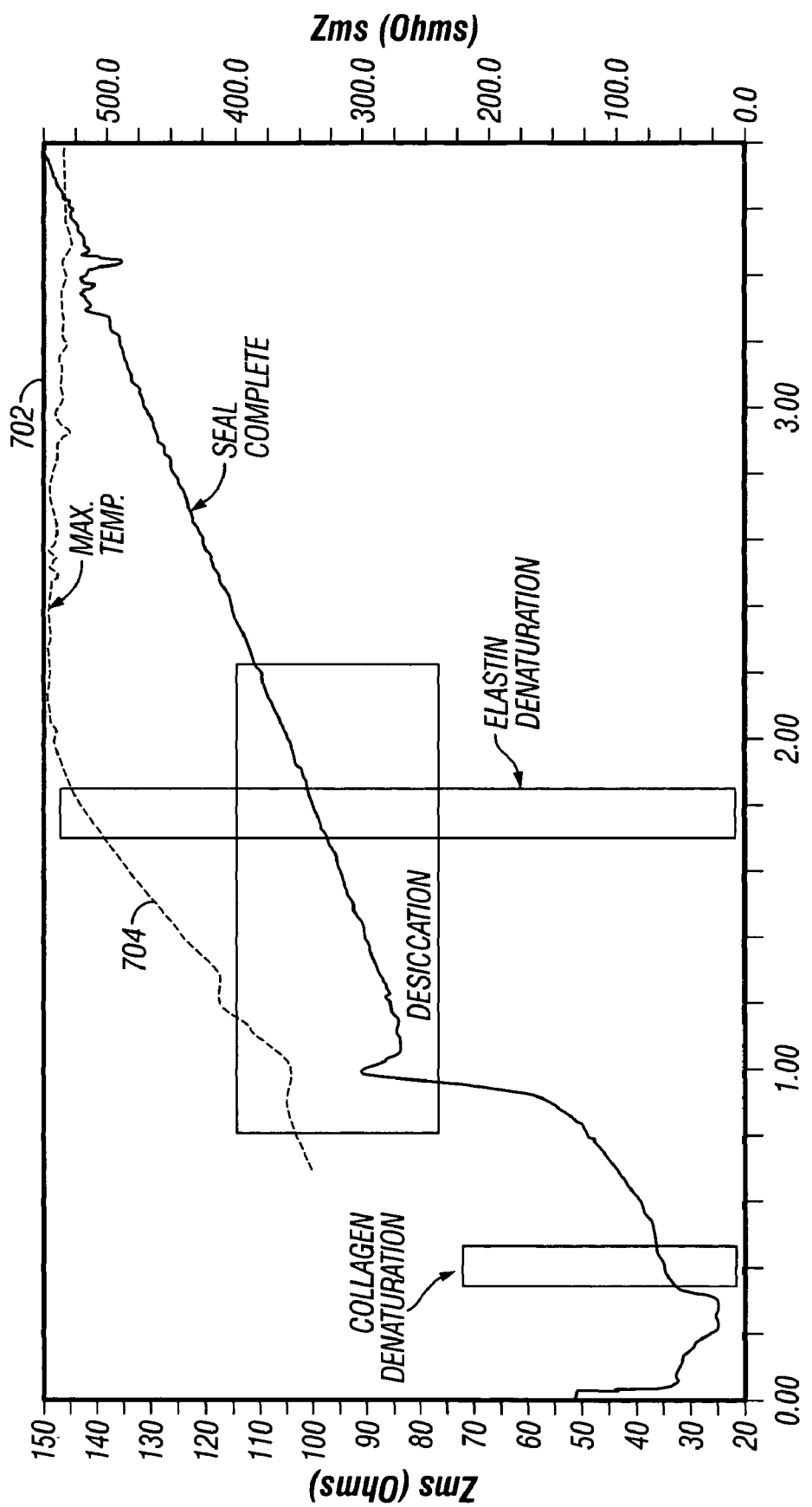
FIG. 7 shows the profile of a temperature graph wherein the tissue impedance is driven along an ideal impedance curve with annotations describing tissue transformation over time as it relates to temperature and impedance.

As can be appreciated, the above-mentioned feedback control system 100 plays an important role in driving the impedance response along the ideal impedance curve to optimize tissue fusion. By continually monitoring tissue impedance response over the course of the tissue fusion process, the energy delivery may be efficiently and accurately controlled to correspond to the biological events of the tissue and drive the sealing process along the ideal impedance curve 500. FIG. 7 shows an impedance profile 702 and a corresponding temperature profile 704 of tissue during a sealing procedure, wherein the impedance is driven along an ideal impedance curve. As shown in FIG. 7, certain biological events occur within the tissue during the sealing process with respect to both impedance and temperature, e.g., collagen denaturization, water vaporization, desiccation, elastin denaturization and collagen and elastin reformation. As can be appreciated, these biological changes in the tissue lead to variations in tissue impedance and tissue temperature over time. Moreover, as each of these biological events occurs through the sealing process, the energy delivered to the tissue has different effects on the tissue.

Figure 6A:
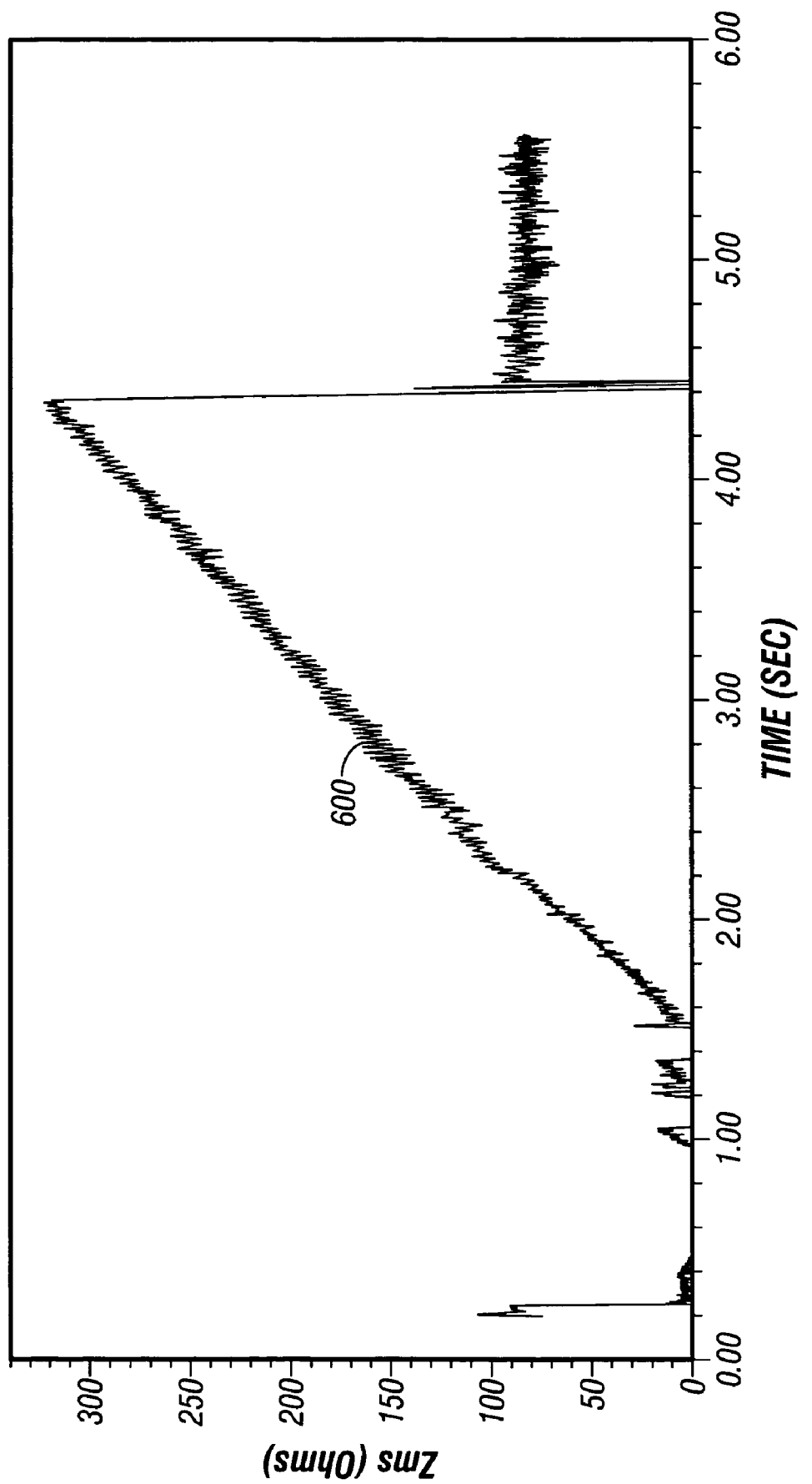
FIG. 6A is an actual graph showing the impedance over time for sealing a large soft tissue structure wherein the impedance is driven along an ideal impedance curve.
Figure 6B:
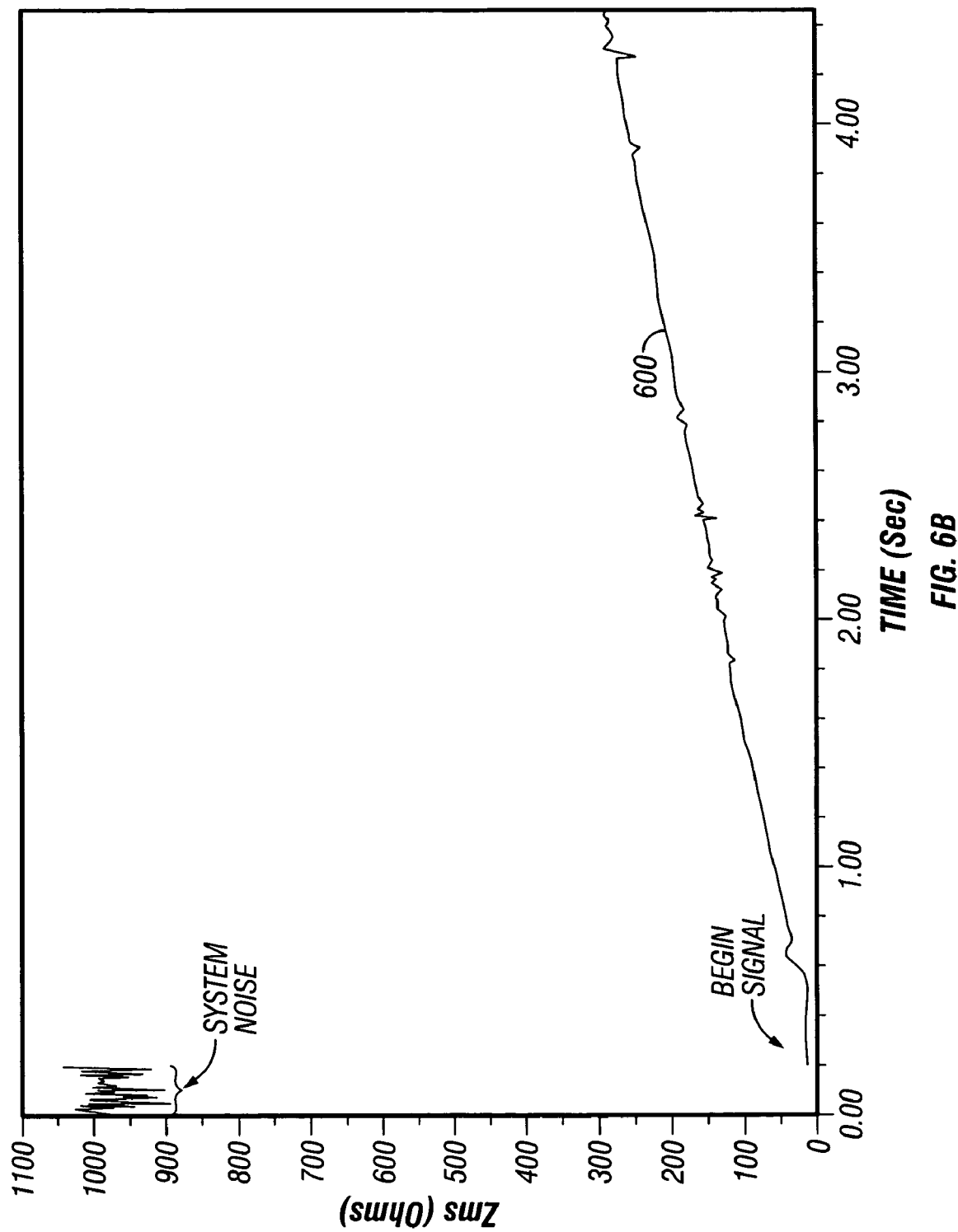
FIG. 6B is another actual graph showing the impedance over time for sealing a large soft tissue structure, wherein the impedance is driven along an ideal impedance curve.

By continually monitoring the tissue impedance response and/or temperature response over time by the control module 102, the energy delivered to the patient may be effectively controlled to drive the impedance response along an ideal curve to optimize sealing. An example of an actual impedance curve 600 driven along an ideal impedance curve for a large soft tissue structure is shown in FIGS. 6A and 6B, where optimal rates for dz/dt are shown substantially between 25-500 ohms/sec, and preferably substantially between 50-150 ohms/sec. As can be appreciated by the present disclosure, driving the tissue sealing process along an ideal impedance curve in accordance with sensed tissue response enables many different types of tissue having many different thicknesses to be effectively sealed without manual intervention.

The trajectory method may be used here for driving the impedance along the impedance curve, including controlling dz/dt (the slope of the line plotted for real-time Z(Zrt) vs. time) by monitoring dz/dt and controlling the energy delivery. Using the trajectory method, a target line for desired Z vs. time (t) is provided which is an approximation of an ideal curve. The target line is obtained via a mapping, e.g., a continuous value mapping, a look up table, a formula, etc. The target line has a slope that is a target slope, e.g., target dz/dt. Zrt is sensed at time (t), and the desired value for Z (Zd) is determined by accessing the value for Zd on the desired line at time (t). Zrt is compared to Zd and the energy output (I, V and/or P) is adjusted in accordance with the magnitude of the differential. An exemplary target line 510 approximating ideal curve 500 having a target slope is shown in FIG. 5. During stage 2, the impedance curve is driven to have a slope that matches the target slope. It is contemplated that different target lines (having respective target slopes) may be selected and used at different stages of a surgical procedure. As transition from a first stage to a second stage is recognized, an appropriate target line that corresponds to the second stage is used.

Similarly, tissue temperature response may be controlled by monitoring dT/dt, including providing and consulting a target line for desired T plotted vs. time (t) having a target slope, target dT/dt. Real time measurements taken at time (t) are compared to desired values for T at the corresponding time (t), and adjustments to the energy output are made in accordance with the magnitude of the differential.

It is envisioned that the tissue may also be effectively sealed by driving the tissue response along an ideal temperature curve (not shown). The control module 102 may control the energy delivery to the tissue such that the tissue response is forced along an ideal temperature curve which is known to produce effective and reliable tissue seals. Although the surgical energy is preferably delivered as high voltage ratio frequency, such as via a mapping, e.g., a continuous value mapping, a look up table or a formula, where the target line has a slope that is a target slope, e.g., target dz/dt, to produce the tissue seal, it is contemplated that other energy sources know in the art may also be utilized to drive the tissue response along an ideal impedance and/or temperature curves, e.g., resistive heat energy, ultrasonic, light, laser, etc.

The embodiments described for controlling generation of surgical energy are capable of providing consistent tissue effect which may include uniform sealing of tissue when desired, e.g., which may include normalizing tissue properties in terms of variability, such as tissue hydration, volume and composition, including across a variety of collagen and elastin rich tissues (e.g., lung and intestine).

Closed-loop control during an electrosurgical procedure for sealing tissue as described above enables consistent and reliable tissue fusion by controlling the remodeling of collagen and elastin in soft tissue. The fusion goes beyond vessels and into tissue that had previously seemed unapproachable with RF energy. Regulation of the electrosurgical energy delivered to the patient facilitates denaturing and melting of proteins in the tissue, and regulation of mechanical pressure (by controlling the gap and/or pressure applied by electrodes of the electrosurgical instrument delivering the electrosurgical energy) facilitates mixing of proteins from opposing tissue layers to produce a solid amalgamous mass, resulting in a seal resistant to fluid or air leakage without negative side effects, such as tissue fragmentation or thermal spread.

Although this disclosure has been described with respect to preferred embodiments, it will be readily apparent to those having ordinary skill in the art to which it appertains that changes and modifications may be made thereto without departing from the spirit or scope of the disclosure. For example, it is envisioned that other generators are used instead of or in addition to the generator described above, such as an ultrasound generator, laser generator and/or a resistive heat generator.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. An electrosurgical generator configured to generate electrosurgical energy delivered to a patient for performing an electrosurgical procedure for sealing tissue, the generator comprising:
   at least one sensor configured to sense at least one of a physical and electrical property related to the delivery of the electrosurgical energy;
   at least one processor configured to receive sensed data corresponding to the at least one of the physical and electrical property and to process at least a portion of said received sensed data to control the electrosurgical generator, the at least one processor further configured to continuously compare the received sensed data to a mapping having a time-based plot of desired progression of the at least one of the physical and electrical property, the at least one processor configured to generate at least one control signal as a function of the comparison of the sensed data with the mapping for regulating electrosurgical energy output from said electrosurgical generator; and
   the at least one processor including a first control module for controlling an inner control loop for controlling the electrosurgical generator in accordance with a first mapping of the mapping and a second control module for controlling an outer control loop for controlling the second control module in accordance with a second mapping of the mapping.

2. The electrosurgical generator according to claim 1, wherein the at least one processor determines a differential between the sensed data and a corresponding point of the time-based plot of desired progression of the at least one of the physical and electrical property and a target value and wherein the at least one processor controls the electrosurgical generator in accordance with the determined differential.

3. The electrosurgical generator according to claim 1, wherein the mapping is selected from the group of mappings consisting of a look-up table, a function and a continuous value mapping.

4. The electrosurgical generator according to claim 1, wherein the at least one of the physical and electrical property is selected from the group of properties consisting of temperature, impedance, current, power and voltage of the tissue proximate the surgical site.

5. The electrosurgical generator according to claim 1, wherein the at least one processor is further configured to receive and process additional data and generate the at least one control signal in accordance with the received and processed additional data, wherein the additional data is selected from at least one of an actual optical characteristic of tissue proximate the surgical site selected from the group of characteristics consisting of absorption properties, reflectivity properties, transmissivity properties and opaqueness properties, actual volume of tissue between jaws of an electrosurgical instrument delivering the electrosurgical energy, an actual elastomeric property of tissue proximate the surgical site, actual viability of tissue proximate the surgical site, actual pressure reactivity of tissue proximate the surgical site, actual moisture content level of tissue proximate the surgical site; actual thickness of tissue proximate the surgical site, actual gap between electrodes of the electrosurgical instrument, actual pressure applied by the electrosurgical instrument, actual leakage current, a desired optical characteristic of tissue proximate the surgical site selected from the group of characteristics consisting of absorption properties, reflectivity properties, transmissivity properties and opaqueness properties, desired volume of tissue between jaws of the electrosurgical instrument, a desired elastomeric property of tissue proximate the surgical site, desired viability of tissue proximate the surgical site, desired viability of sealed tissue, desired pressure reactivity of tissue proximate the surgical site, desired moisture content level of tissue proximate the surgical site; desired thickness of tissue proximate the surgical site, desired gap between electrodes of the electrosurgical instrument, desired pressure applied by the electrosurgical instrument type of electrosurgical instrument, type of tissue being sealed, patient profile data, patient's disease profile data, at least one mapping of the at least one mapping, allowed leakage current, applied voltage, applied current, at least one predetermined threshold value and at least one target parameter for a corresponding parameter of the electrosurgical energy.

6. The electrosurgical generator according to claim 5, wherein the at least one processor is further configured to determine a change in values of the data over a variable, a rate of change of the data over the variable, and a change of rate of change of the data over the variable, and to determine when an event has occurred, the event being selected from the group of events consisting of exceeding a predetermined threshold value by the data, by the change in values of the data over the variable, by the rate of change of the data over the variable, by the change of the rate of change of the data over the variable, by a difference between the data and a predetermined value, by a determined seal quality value, by a determined seal completion value, by a difference between the sensed data and a corresponding target value obtained from the at least one mapping, and by a timing value generated by a timing device.

7. The electrosurgical generator according to claim 6, wherein the at least one processor is further configured to determine when the quality of a seal is below a predetermined threshold level, and upon determining that the seal quality is below the predetermined threshold level the at least one processor initiates a new electrosurgical procedure for sealing tissue.

8. The electrosurgical generator according to claim 7, wherein the initiating the new electrosurgical procedure includes using at least one of the sensed data and parameter settings of the electrosurgical energy from the previous procedure for controlling the electrosurgical generator for the new procedure.

9. The electrosurgical generator according to claim 6, further comprising an indicator device configured to indicate to an operator at least one of the determined seal quality, and a representation of a comparison of the sensed data with the mapping.

10. The electrosurgical generator according to claim 5, wherein the at least one processor is further configured to determine imminent damage to tissue proximate the surgical site, actual damage to tissue proximate the surgical site, imminent thermal spread to tissue proximate the surgical site, and actual thermal spread to tissue proximate the surgical site.

11. The electrosurgical generator according to claim 10, wherein upon determining at least one of the imminent damage, the actual damage, the imminent thermal spread, and the actual thermal spread, the at least one processor performs at least one of controlling the electrosurgical generator for regulating the output of the electrosurgical generator by at least one of reducing output electrosurgical energy and discontinuing output of electrosurgical energy and generating at least one additional control signal for controlling an indicator device for notifying an operator.

12. The electrosurgical generator according to claim 5, wherein the additional data is at least one of sensed and user entered.

13. The electrosurgical generator according to claim 5, wherein the additional data is at least one of received and processed at a pre-surgical time before beginning the electrosurgical procedure and a concurrent-surgical time during the electrosurgical procedure.

14. The electrosurgical generator according to claim 5, wherein the at least one processor is further configured to determine the tissue type.

15. The electrosurgical generator according to claim 5, wherein at least one of the received sensed data and additional data is received at a pre-surgical time before beginning the procedure, and the at least one of the received sensed data and additional data responds to application of a pre-surgical electrosurgical energy applied before beginning the electrosurgical procedure.

16. The electrosurgical generator according to claim 5, wherein the at least one processor is further configured to control the electrosurgical energy by initializing parameters of the electrosurgical energy before beginning the electrosurgical procedure.

17. The electrosurgical generator according to claim 1, wherein mapping includes a continuous value mapping having a target curve plotted over a variable, wherein at a respective point on the target curve the target curve has a target slope and during the procedure a rate of change of the sensed data is compared to the target slope for a respective point on the target curve that corresponds to a condition of the variable when the data was sensed, and the controlling of the electrosurgical generator is in accordance with the results of the comparison.

18. The electrosurgical generator according to claim 17, wherein the target curve includes at least a first stage having a first target slope and second stage having a second target slope, and the first and second target slopes are different, and the controlling of the electrosurgical generator includes changing control from controlling in accordance with the first stage to controlling in accordance with the second stage when an occurrence of an event has been recognized.

19. The electrosurgical generator according to claim 1, wherein the at least one processor is further configured to regulate parameters of the electrosurgical energy selected from the group of parameters consisting of voltage, current, resistance, intensity, power, frequency, amplitude, and pulse parameters, wherein the pulse parameters are selected from the group of pulse parameters consisting of pulse width, duty cycle, crest factor, and repetition rate.

20. An electrosurgical generator configured to generate electrosurgical energy delivered to a patient for performing an electrosurgical procedure for sealing tissue, the generator comprising:

at least one sensor configured to sense at least one of a physical and electrical property related to the delivery of the electrosurgical energy;

at least one processor configured to receive sensed data corresponding to the at least one of the physical and electrical property and to process at least a portion of said received sensed data to control the electrosurgical generator, the at least one processor further configured to continuously compare the received sensed data to a mapping having a time-based plot of desired progression of the at least one of the physical and electrical property, the at least one processor configured to generate at least one control signal as a function of the comparison of the sensed data with the mapping for regulating electrosurgical energy output from said electrosurgical generator;

the at least one processor further configured to receive and process additional data and generate the at least one control signal in accordance with the received and processed additional data, wherein the additional data is selected from at least one of an actual optical characteristic of tissue proximate the surgical site selected from the group of characteristics consisting of absorption properties, reflectivity properties, transmissivity properties and opaqueness properties, actual volume of tissue between jaws of an electrosurgical instrument delivering the electrosurgical energy, an actual elastomeric property of tissue proximate the surgical site, actual viability of tissue proximate the surgical site, actual pressure reactivity of tissue proximate the surgical site, actual moisture content level of tissue proximate the surgical site; actual thickness of tissue proximate the surgical site, actual gap between electrodes of the electrosurgical instrument, actual pressure applied by the electrosurgical instrument, actual leakage current, a desired optical characteristic of tissue proximate the surgical site selected from the group of characteristics consisting of absorption properties, reflectivity properties, transmissivity properties and opaqueness properties, desired volume of tissue between jaws of the electrosurgical instrument, a desired elastomeric property of tissue proximate the surgical site, desired viability of tissue proximate the surgical site, desired viability of sealed tissue, desired pressure reactivity of tissue proximate the surgical site, desired moisture content level of tissue proximate the surgical site; desired thickness of tissue proximate the surgical site, desired gap between electrodes of the electrosurgical instrument, desired pressure applied by the electrosurgical instrument type of electrosurgical instrument, type of tissue being sealed, patient profile data, patient's disease profile data, at least one mapping of the at least one mapping, allowed leakage current, applied voltage, applied current, at least one predetermined threshold value and at least one target parameter for a corresponding parameter of the electrosurgical energy;

the at least one processor further configured to determine a change in values of the data over a variable a rate of change of the data over the variable and a change of rate of change of the data over the variable, and to determine when an event has occurred, the event being selected from the group of events consisting of exceeding a predetermined threshold value by the data, by the change in values of the data over the variable, by the rate of change of the data over the variable, by the change of the rate of change of the data over the variable, by a difference between the data and a predetermined value, by a determined seal quality value, by a determined seal completion value, by a difference between the sensed data and a corresponding target value obtained from the at least one mapping, and by a timing value generated by a timing device; and the at least one processor further configured to determine when the quality of a seal is below a predetermined threshold level, and upon determining that the seal quality is below the predetermined threshold level the at least one processor initiates a new electrosurgical procedure for sealing tissue.

21. The electrosurgical generator according to claim 20, wherein the mapping is selected from the group of mappings consisting of a look-up table, a function and a continuous value mapping.

22. The electrosurgical generator according to claim 20, wherein the at least one of the physical and electrical property is selected from the group of properties consisting of temperature, impedance, current, power and voltage of the tissue proximate the surgical site.

23. The electrosurgical generator according to claim 20, wherein the at least one processor is further configured to determine imminent damage to tissue proximate the surgical site, actual damage to tissue proximate the surgical site, imminent thermal spread to tissue proximate the surgical site, and actual thermal spread to tissue proximate the surgical site.

24. The electrosurgical generator according to claim 23, wherein upon determining at least one of the imminent damage, the actual damage, the imminent thermal spread, and the actual thermal spread, the at least one processor performs at least one of controlling the electrosurgical generator for regulating the output of the electrosurgical generator by at least one of reducing output electrosurgical energy and discontinuing output of electrosurgical energy and generating at least one additional control signal for controlling an indicator device for notifying an operator.

25. The electrosurgical generator according to claim 20, wherein the additional data is at least one of sensed and user entered.

26. The electrosurgical generator according to claim 20, wherein the additional data is at least one of received and processed at a pre-surgical time before beginning the electrosurgical procedure and a concurrent-surgical time during the electrosurgical procedure.

27. The electrosurgical generator according to claim 20, wherein mapping includes a continuous value mapping having a target curve plotted over a variable, wherein at a respective point on the target curve the target curve has a target slope and during the procedure a rate of change of the sensed data is compared to the target slope for a respective point on the target curve that corresponds to a condition of the variable when the data was sensed, and the controlling of the electrosurgical generator is in accordance with the results of the comparison.

28. The electrosurgical generator according to claim 27, wherein the target curve includes at least a first stage having a first target slope and second stage having a second target slope, and the first and second target slopes are different, and the controlling of the electrosurgical generator includes changing control from controlling in accordance with the first stage to controlling in accordance with the second stage when an occurrence of an event has been recognized.

29. The electrosurgical generator according to claim 20, wherein the at least one processor is further configured to determine the tissue type.

30. The electrosurgical generator according to claim 20, wherein at least one of the received sensed data and additional data is received at a pre-surgical time before beginning the procedure, and the at least one of the received sensed data and additional data responds to application of a pre-surgical electrosurgical energy applied before beginning the electrosurgical procedure.

31. The electrosurgical generator according to claim 20, wherein the at least one processor is further configured to control the electrosurgical energy by initializing parameters of the electrosurgical energy before beginning the electrosurgical procedure.

32. The electrosurgical generator according to claim 20, wherein the initiating the new electrosurgical procedure includes using at least one of the sensed data and parameter settings of the electrosurgical energy from the previous procedure for controlling the electrosurgical generator for the new procedure.

33. The electrosurgical generator according to claim 20, further comprising an indicator device configured to indicate to an operator at least one of the determined seal quality, and a representation of a comparison of the sensed data with the mapping.

34. The electrosurgical generator according to claim 20, wherein the at least one processor is further configured to regulate parameters of the electrosurgical energy selected from the group of parameters consisting of voltage, current, resistance, intensity, power, frequency, amplitude, and pulse parameters, wherein the pulse parameters are selected from the group of pulse parameters consisting of pulse width, duty cycle, crest factor, and repetition rate.

35. The electrosurgical generator according to claim 20, wherein the at least one processor is further configured to select at least one mapping from a plurality of accessible mappings.

* * * * *